United States Patent
Duke et al.

(10) Patent No.: US 8,774,889 B2
(45) Date of Patent: Jul. 8, 2014

(54) PATIENT MONITORING SYSTEM WITH EFFICIENT PATTERN MATCHING ALGORITHM

(75) Inventors: David Duke, Fishers, IN (US); Abhishek S. Soni, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 729 days.

(21) Appl. No.: 12/975,654

(22) Filed: Dec. 22, 2010

(65) Prior Publication Data

US 2012/0165638 A1 Jun. 28, 2012

(51) Int. Cl.
*A61B 5/05* (2006.01)

(52) U.S. Cl.
USPC .............................. 600/345; 600/347; 600/365

(58) Field of Classification Search
USPC ........ 600/309, 316, 345–347, 365; 435/4, 14; 436/68; 422/50, 420–429; 204/403.01–403.15; 702/23; 604/64–66; 606/167, 181–183
See application file for complete search history.

(56) References Cited

U.S. PATENT DOCUMENTS

| | | | |
|---|---|---|---|
| 4,660,151 A * | 4/1987 | Chipman et al. | 702/23 |
| 5,339,826 A * | 8/1994 | Schmidt et al. | 600/544 |
| 2004/0127777 A1 * | 7/2004 | Ruchti et al. | 600/316 |
| 2007/0179367 A1 * | 8/2007 | Ruchti et al. | 600/310 |
| 2008/0073443 A1 | 3/2008 | Tollens et al. | |

FOREIGN PATENT DOCUMENTS

| | | | |
|---|---|---|---|
| EP | 1 918 837 A1 | | 5/2008 |
| EP | 1918837 A1 * | | 5/2008 |

OTHER PUBLICATIONS

Bentley, Multidimensional Binary Search Trees Used for Associative Searching, ACM, vol. 18, No. 9, Sep. 1975, p. 509-517, USA.
Bentley, Multidimensional Divide-and-Conquer, ACM, vol. 23, No. 4, Apr. 1980, p. 214-229, USA.

* cited by examiner

*Primary Examiner* — Michael D'Angelo
(74) *Attorney, Agent, or Firm* — Dinsmore & Shohl, LLP

(57) ABSTRACT

A patient monitoring system with an efficient pattern matching algorithm, a method, and a computer product thereof are disclosed. The system may include a physiological data input device or sensor which receives a plurality of physiological measurements within a time window thereby generating at least one time window data set, a memory which stores a program, and a processor. The program when executed by the processor, causes the processor to compress the at least one time window data set to a reduced-rank basis, and perform a pattern match between a reference pattern and the compressed at least one time window data set using a distance metric.

8 Claims, 17 Drawing Sheets

PATIENT MONITORING SYSTEM WITH EFFICIENT PATTERN MATCHING ALGORITHM

TECHNICAL FIELD

The following disclosure relates generally to patient monitoring, and in particular to a continuous glucose monitoring system with an efficient pattern matching algorithm, a method, and a computer product thereof.

BACKGROUND

Diabetes can be characterized by hyperglycemia and relative insulin deficiency. There are two main types of diabetes, Type I diabetes (insulin-dependent diabetes mellitus) and Type II diabetes (non-insulin-dependent diabetes mellitus). In some instances, diabetes is also characterized by insulin resistance.

Insulin secretion functions to control the level of blood glucose to keep the glucose levels at an optimum level. Healthcare may involve both establishing a therapeutic program and monitoring the progress of the afflicted person. Monitoring blood glucose levels is an important process that is used to help diabetics maintain blood glucose levels as near as normal as possible throughout the day. Monitoring can also allow successful treatment of a diabetic by altering therapy as necessary. Monitoring may allow the diabetic to monitor more closely his or her condition and, in addition, can provide information of value to the healthcare provider in determining both progress of the patient and detecting any need to change the patient's therapy program.

Advances in the field of electronics over the past several years have brought about significant changes in medical diagnostic and monitoring equipment, including self-care monitoring. In controlling and monitoring diabetes, relatively inexpensive and easy-to-use blood glucose monitoring systems have become available that provide reliable information that allows a diabetic and his or her healthcare professional to establish, monitor and adjust a treatment plan.

There are two main types of blood glucose monitoring systems used by patients: single point (or non-continuous) systems and continuous systems. Non-continuous systems consist of meters and tests strips and require blood samples to be drawn from fingertips or alternate sites, such as forearms and legs. An example of a non-continuous system may require a diabetic to apply a blood sample to reagent-impregnated region of a test strip, wipe the blood sample from the test strip after a predetermined period of time, and, after a second predetermined period of time, determine blood glucose level by comparing the color of the reagent-impregnated regions of the test strip with a color chart supplied by the test strip manufacturer. These systems also can rely on lancing and manipulation of the fingers or alternate blood draw sites, which can be extremely painful and inconvenient, particularly for children.

An example of a continuous system is a continuous glucose monitors ("CGM") that can be implanted subcutaneously and measure glucose levels in the interstitial fluid at various periods throughout the day, providing data that shows trends in glucose measurements over a period of time. CGMs can provide large quantities of similar data that need to be processed to find patterns of similar data. The data can be used to identify harmful patient behaviors or to help optimize therapy based on similar past experiences. It can also be used to monitor glucose over time to determine a blood sugar pattern. Because of the large quantities of data involved, an efficient algorithm may be needed to enable pattern matching on devices with limited processing power.

While a variety of devices and techniques may exist for continuously monitoring a patient over time, it is believed that no one prior to the inventors has made or used the inventive embodiments as described herein.

SUMMARY

In one example, a patient monitoring system is disclosed. The system may comprise: a physiological data input device which acquires a plurality of physiological measurements of the patient within a time window thereby generating at least one time window data set; a memory storing a pattern matching algorithm; a database to store the at least one time window data set; and a processor in communication with said input device to receive said generated at least one time window data set, and in communication with said memory in order to execute said pattern matching algorithm. The pattern matching algorithm when executed by said processor causes said processor to compress the at least one time window data set, store the compressed at least one time window data set, and perform a pattern match between a reference pattern and the stored at least one time window data set using a distance metric provided by the pattern matching algorithm.

In another example, a non-transitory computer-readable medium is disclosed that stores a program that, when executed by a processor, causes the processor to perform at least a pattern match between a reference pattern and at least one stored time window data set collected via a patient monitoring system using a distance metric.

In still another example, a method for identifying a diabetes-related event in a patient using a patient monitoring system comprising a physiological data input device and a processor is disclosed. The method comprises receiving automatically from the physiological data input device at least one time window data set indicative of a physiological measurement related to the diabetes-related event; associating automatically using the processor the at least one time window data set with a data tag; transforming automatically using the processor the associated at least one time window data set into a normalized at least one time window data set, wherein the normalized at least one time window data set has a mean of zero and a standard deviation of one, compressing automatically using the processor the normalized at least one time window data set into a compressed at least one time window data set, and pattern matching, automatically using the processor, between a reference pattern and the compressed at least one time window data set using a distance metric.

In still another example, a method for real-time identification of a diabetes-related event in a patient using a patient monitoring system comprising a physiological data input device, a user input device and a processor is disclosed. The method comprises receiving automatically from the user input device at least one reference pattern and associated alert signal; receiving automatically from the physiological data input device at least one time window data set indicative of a physiological measurement related to the diabetes-related event; associating automatically using the processor the at least one time window data set with a data tag; transforming automatically using the processor the associated at least one time window data set into a normalized at least one time window data set, wherein the normalized at least one time window data set has a mean of zero and a standard deviation of one; compressing automatically using the processor the normalized at least one time window data set into a compressed at least one time window data set; storing automatically using the processor the compressed at least one time window data set; and pattern matching automatically using the processor between the reference pattern and the stored at least one time window data set using a distance metric, wherein when the distance metric is less than ϵ, the processor automatically triggers the alert.

While the specification concludes with claims, which particularly point out and distinctly claim the invention, it is believed the present invention will be better understood from the following description of certain examples taken in conjunction with the accompanying drawings. In the drawings, like numerals represent like elements throughout the several views.

Figure 1:
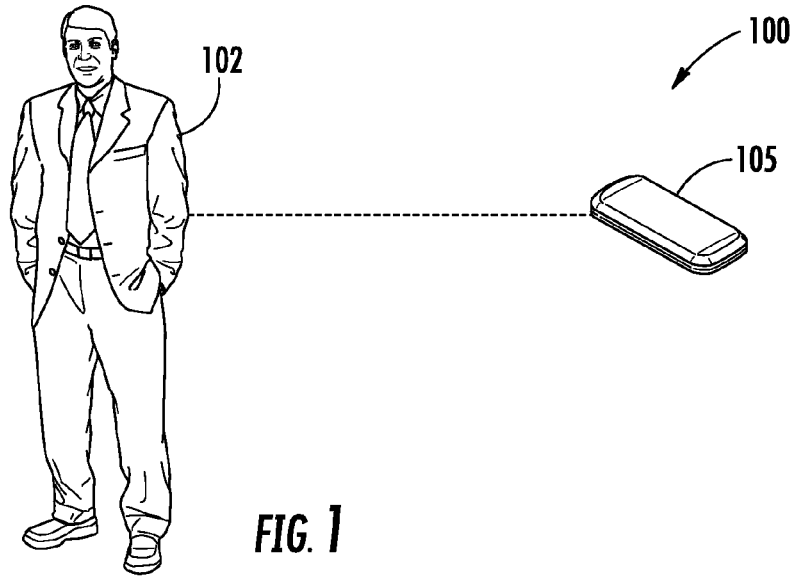
FIG. 1 depicts a diagram of an exemplary version of a patient monitoring system associated with a diabetic patient.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

Exemplary Devices and Methods

FIG. 1 depicts an exemplary configuration of a patient monitoring system 100 in association with a patient 102. The patient 102 may be a diabetic patient, or a patient with a physiological condition which requires routine or continuous monitoring. The monitoring system 100 comprises hardware and software components that may be utilized for implementing a pattern matching feature as described further herein. As illustrated, the monitoring system 100 comprises a device 105. Device 105 may be a handheld system with limited processing power, such as a PDA, mobile phone, glucose meter, etc. Device 105 may also be a personal computer. As further shown in FIG. 2, device 105 may comprise a physiological data input device(s) 110, a data interface 115, a processor 120, a database 130, a memory 135 along with analysis logic 132, and a display 140. These components are "operably connected" to each other, which may include one or more components connected to one or more other components, either directly or through one or more intermediate components such that they may communicate and pass information as needed to perform at least the hereinafter described processes and functions. The connection may be mechanical, electrical connection, or a connection that allows transmission of signals between the components, e.g., wired or wirelessly. The device 105 may further include an input mechanism or user interface 145 to input information and/or make data/output requests. Exemplary input mechanisms or user interfaces 145 may include a touch screen, input buttons, a keyboard, a mouse, a microphone, and combinations thereof. In one embodiment, the patient monitoring system 100 enables continuous glucose monitoring in which device 105 is operable to take multiple measurements of a concentration of glucose or a substance indicative of the concentration or presence of glucose via the physiological data input device 110, and process that dataset using the processor 120 to find similar patterns. As used herein, continuous (or continual) glucose monitor (or monitoring) may include the period in which monitoring of glucose concentration is continuously, continually, and/or intermittently (e.g., regularly or irregularly) performed.

Figure 2:
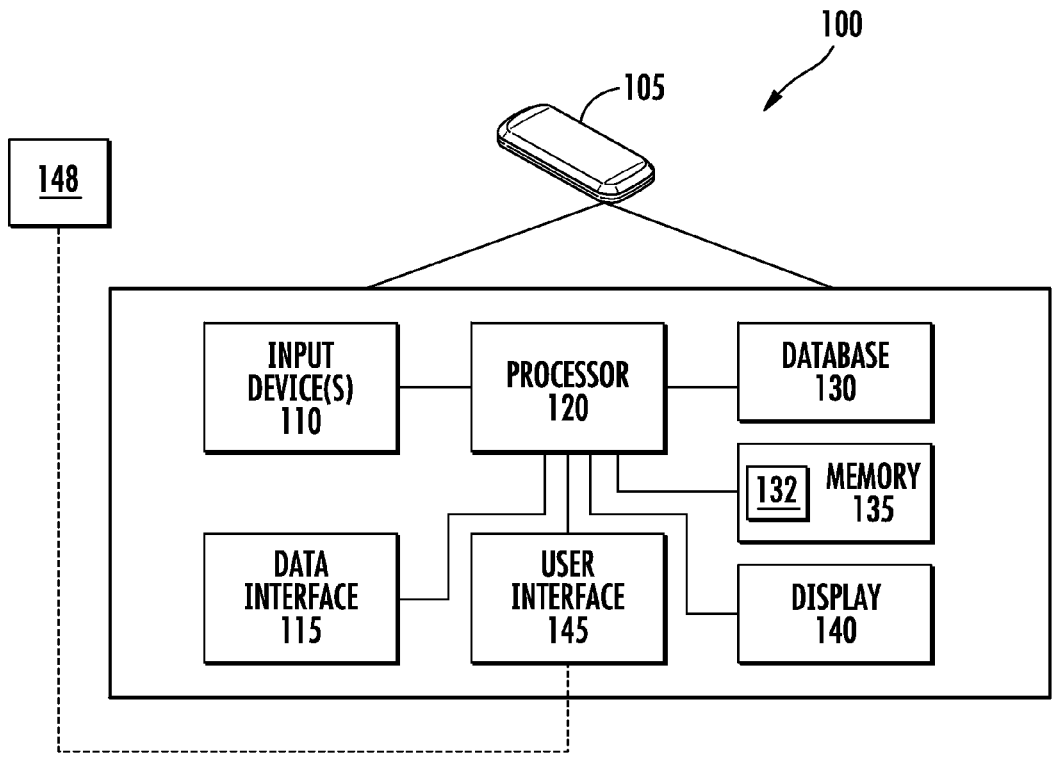
FIG. 2 depicts a block diagram of the exemplary version of the patient monitoring system of FIG. 1.

Referring to FIG. 2, the physiological data input device 110 may be, e.g., in one embodiment one or more sensors which gather automatically patient-specific physiological data such as, e.g., blood glucose, blood viscosity or other information concerning the blood chemistry of the patent 102, physical activity, temperature, heart rate, blood pressure, breathing pattern, other patient-specific physiological parameters, and combinations thereof. In one embodiment, the physiological data input device 110 can be a component or region of a patient monitoring system 100 by which glucose can be quantified and configured to produce a signal indicative of a glucose concentration of the patient 102. In operation, the physiological data input device 110 may by a glucose sensor which measures and acquires a detectable signal (e.g., a chemical signal, electrochemical signal, etc.), either directly or indirectly, from glucose or derivatives thereof that are indicative of the concentration or presence of glucose and then may transmit the signal to the processor 120 for further processing and/or storage in database 130. The physiological data input device 110 may be in communication with processor 120.

As used herein, the physiological data input device 110 may be a continuous device, for example, a subcutaneous, transdermal (e.g., transcutaneous), or intravascular device. However, it should be understood that the devices and methods described herein can be applied to any device (including external devices) capable of detecting a concentration of glucose and providing an output signal that represents the concentration of glucose. The physiological data input device 110 in another embodiment can be hardware and/or software which can analyze a plurality of intermittent biological samples, for example, blood, interstitial fluid, other desired biological fluid, etc. The physiological data input device 110 can use any method of glucose-sensing, including enzymatic, chemical, physical, electrochemical, spectrophotometric, polarimetric, calorimetric, radiometric, etc. The physiological data input device 110 may use any method, including invasive, minimally invasive, and non-invasive sensing techniques, to provide an output signal indicative of, e.g., the glucose concentration or other physiological data. The output signal can be a raw data measurement that is used to provide a useful value of glucose to a user, such as a patient or physician, who may be using the device. Smoothing, evaluation methods, etc. may be applied to the raw data measurement to provide transformed data measurements to the user.

Data measurements may be derived from the intermittent collection of data comprising measurements made by a device, such as e.g., the physiological data input device 110, (for example, a current measurement that ultimately corresponds to a glucose amount or concentration). The data measurements may be further associated with relevant data tags. By way of example only, a data tag may include when a meal was eaten, insulin was given, exercise took place, etc. Additionally, a data tag may include the amount of nutritional content in a meal, insulin, oral medication, exercise, etc. The data measurements may further comprise determining transformed data measurements from one or more raw data measurements and associating those transformed data measurements with relevant data tags.

The data measurements are obtained from a particular biological system (e.g., blood, interstitial fluid, etc.) using a device, such as e.g., the physiological data input device 110, maintained in operative contact with the biological system over a time window. The time window may be a defined period of time (e.g., hour(s), day(s), etc.) to obtain a series of data measurements (e.g., second(s), minute(s), hour(s), etc.) resulting in at least one time window dataset. The time window may be started and stopped by the diabetic patient 102 as well. By way of example only, the diabetic patient 102 may start the time window at the beginning of a meal and stop the time window at some later date after the meal. The at least one time window data set (or data measurements) may be collected from a single individual. Alternatively, the at least one time window data set (or data measurements) may be collected from multiple individuals and compiled into a database, at either the time the at least one time window data set (or data measurements) were collected or subsequently. The at least one time window data set may include raw data measurements, transformed data measurements, raw or transformed data measurements associated with data tags, or a combination thereof from the sensor.

The physiological data input device 110 may be capable of measuring only glucose in one embodiment. Alternately, in other embodiments, the physiological data input device 110 may be capable of measuring any other physiological analyte of interest that is a specific substance or component that is being detected and/or measured by chemical, physical, enzymatic, or optical analysis. The data measurements for each physiological analyte is collected and compiled into a multi-analyte database such as, e.g., database 130. In another example, the database 130 can also be formulated by compiling data measurements collected using multiple monitors, each of which measures a single substance, resulting in the multi-analyte database.

Examples of physiological analytes can include any specific substance, component, or combinations thereof that one is desirous of detecting and/or measuring in a chemical, physical, enzymatic, or optical analysis. Such physiological analytes include, but are not limited to, urate/uric acid, glucose, urea (blood urea nitrogen), lactate and/or lactic acid, hydroxybutyrate, cholesterol, triglycerides, creatine, creatinine, insulin, hematocrit, and hemoglobin), carbonate, calcium, potassium, sodium, chloride, bicarbonate, blood gases (e.g., carbon dioxide, oxygen, etc.), heavy metals (e.g., lead, copper, etc.), lipids, amino acids, enzyme substrates or products indicating a disease state or condition, other markers of disease states or conditions, etc. In the case of multi-analyte data databases, all of the physiological analytes may be related to a single physiologic state or condition; alternatively, in other embodiments, each physiological analyte may be relevant to a different physiological state or condition.

In still other embodiments, one or more of the above described physiological data/information may be entered manually by the patient 102, as well as requested for output (e.g., displayed on display 140, sent to another external device via data interface 115, etc.), via the user interface 145. In still other embodiments, the input device 110 may also include, for example, a controller, microcontroller, processor, microprocessor, etc. that is configured to receive and/or process signals, communicate with processor 120, and generate a reference pattern. The reference pattern can be the most recent data set (e.g., the most recent at least one time window data set gathered by the input device 110, a data set from the current day, hour(s), minute(s), etc. provided in memory 135 and/or database 130) and/or for any other data set of interest, e.g., historical data (previous day(s), week(s), month(s), year(s), etc.) of the patient 102. The data set can be provided from the input device 110, the database 130, the memory 135, the user interface 145, and/or from any another external source of patient data that the device 105 may communicate with via the data interface 115. It is to be appreciated that as such the reference pattern can be generated from any of the data available to the device 105, and by any method performed by the processor 120, the input device 110 (if provided with processing means), or an external device(s) operating on the data (and provided to the device via the data interface 115), in which to provide a pattern of interest, such as e.g., a glucose curve. Exemplary methods for generating a glucose curve may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The reference pattern can also be generated from data resulting from a query inputted via the user interface 145 and run by the processor 120 on recent data gathered by the input device 110 or stored data provided in database 130, memory 135 and/or in other external sources that were queried by the processor 120 via data interface 115. The reference pattern may also include any relevant data tags or multi-analyte data, and the generated and/or received reference pattern may be stored in the database 130 and/or memory 135 until needed by the processor 120 for a pattern matching process discussed hereafter in a later section.

The data interface 115 may be hardware and/or software which provides the device 105 with the ability to communicate wired and/or wirelessly with other devices and components as discussed hereafter in some embodiments, as well as to read from and write to non-transitory computer-readable products or storage medium, such as non-transitory computer-readable medium 148, in other embodiments. For the purposes of this description, a non-transitory computer readable product or storage medium can be any apparatus that can contain or store, programs and/or code for use by or in connection with processor, apparatus or devices. Examples of a non-transitory computer readable product or storage medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

Still referring to FIG. 2, the processor 120 may include any general purpose processors or any processing component configured to provide, receive and execute a sequence of instructions (such as from the memory 135). For example, processor 120 may perform calculations using at least one time window data set (or data measurements) from the physiological data input device 110 and/or the reference pattern from input device 110 (when provided with processing means), which may also be viewed as a time window data set that is generated by the input device 110. In another example, processor 120 may also compress the at least one time window data set (or data measurements) to a reduced-rank basis as will be described further herein. In another example, processor 120 may perform pattern matching with at least one time window data set (or data measurements) in a reduced-rank space as will be described further herein. Processor 120 may be implemented as a single computing device or a combination of computing devices, e.g., a combination of a digital signal processor and a microprocessor, a plurality of microprocessors, one or more microcontrollers, one or more microprocessors in conjunction with a digital signal processor core, or any other such configuration.

Still referring to FIG. 2, the display 140 may comprise a liquid crystal display ("LCD"), a touch sensitive screen, a web interface, etc. A touch screen or web interface can provide a convenient way to enter various commands and/or select various programmable options. In operation, display 140 can display information, for e.g., at least one time window data set (or data measurements), pattern match results, labeled regions to identify areas of interest, data tag information, reference patterns, etc. By way of example only, the displayed information may comprise at least one time window data set (or data measurements) that may or may not require processing by the display device prior to display. The at least one time window data set (or data measurements) displayed may be raw data, real-time data, transformed data, etc. The display 140 may comprise hardware and/or software including display instructions (e.g., software programming comprising instructions) configured to enable display of the information on display 140 and/or to obtain the information from database 130. The data in the database 130 may be queried and/or displayed by the processor 120 on the display 140.

Exemplary displays 140 in FIGS. 3(*a*)-3(*e*) depict various ways of displaying the different components and/or various data of a pattern-matching process. FIG. 3(*a*) depicts an exemplary display 300 having a reference pattern plot 310. The reference pattern plot 310 includes a plotted reference pattern 312 generated and displayed by the processor 120 from data of the patient 102 provided from the input device 110, memory 135, database 130, and/or external sources via data interface 115 as discussed previously above, which may be at least one time window data set (or data measurements) or results from a query as also discussed previously above. The reference pattern plot 310 may also include a region labeled to identify hypoglycemia 314, hyperglycemia 316, or other areas of interest. Data tags 318 may also be provided, which are shown and provide additional data relevant to the plotted reference pattern 312, for example, meal information, insulin information, exercise information, etc. Shown below reference pattern plot 310 are two pattern match plots 320, 330. Pattern match plots 320, 330 depict the closest pattern matches plotted on individual plots adjacent to reference pattern plot 310. The pattern match plots 320, 330 can be displayed by scrolling through the plots or by performing a dragging operation 325 on a touch sensitive display. The dragging operation 325 can be performed by touching the screen with a finger and then moving the finger in the desired direction on the screen. Additional data 340 can be displayed in a tabular format. The additional data 340 may be relevant to the reference pattern and match, which may include meal information, carbohydrates data, insulin dose data, exercise information, or any other data that may help in evaluating the match.

FIG. 3(*b*) depicts an exemplary display 300 having a reference pattern plot 310. The reference pattern plot 310 includes a plotted reference pattern 312 that may be for at least one time window data set (or data measurements) or for results of a query, and a closest pattern match plot 350 plotted on the same axis as plotted reference pattern 312. The width of the closest pattern match plot 350 and plotted reference pattern 312 are shown identical. Similar to FIG. 3(*a*), a hypoglycemia region 314, a hyperglycemia region 316, data tags 318 and additional data 340 are shown. Also depicted is label 311, which identifies the rank of the current match. The rank is based on how well it compares to the reference pattern 312. The next closest match plot (not pictured) can be displayed by scrolling through the plots or by performing a dragging operation 327 on a touch sensitive display. The dragging operation 327 can be performed by touching the screen with a finger and then moving the finger in the desired direction on the screen.

FIG. 3(*c*) depicts an exemplary display 300 having a reference pattern plot 310. Similar to FIG. 3(*b*), a hypoglycemia region 314, a hyperglycemia region 316, data tags 318 and additional data 340 are shown. As described above, the reference pattern plot 310 includes a plotted reference pattern 312 that may be for at least one time window data set (or data measurements) or for results of a query, and a closest pattern match plot 350 plotted on the same axis as the plotted reference pattern 312. The closest pattern match plot 350 may be extended to display glucose match data 355 immediately after the plotted reference pattern 312 or similarly extended to display glucose match data immediately before the plotted reference pattern 312 or both.

Figure 3A:
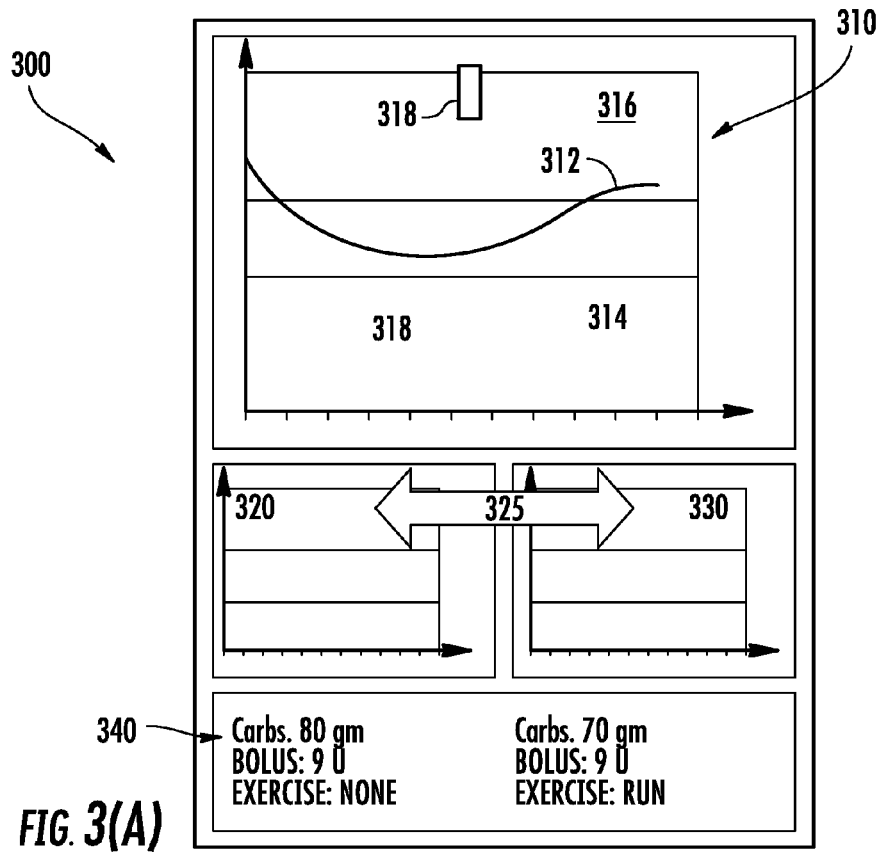
FIGS. 3(a)-3(e) depict exemplary ways of displaying various data of a pattern matching process.
Figure 3B:
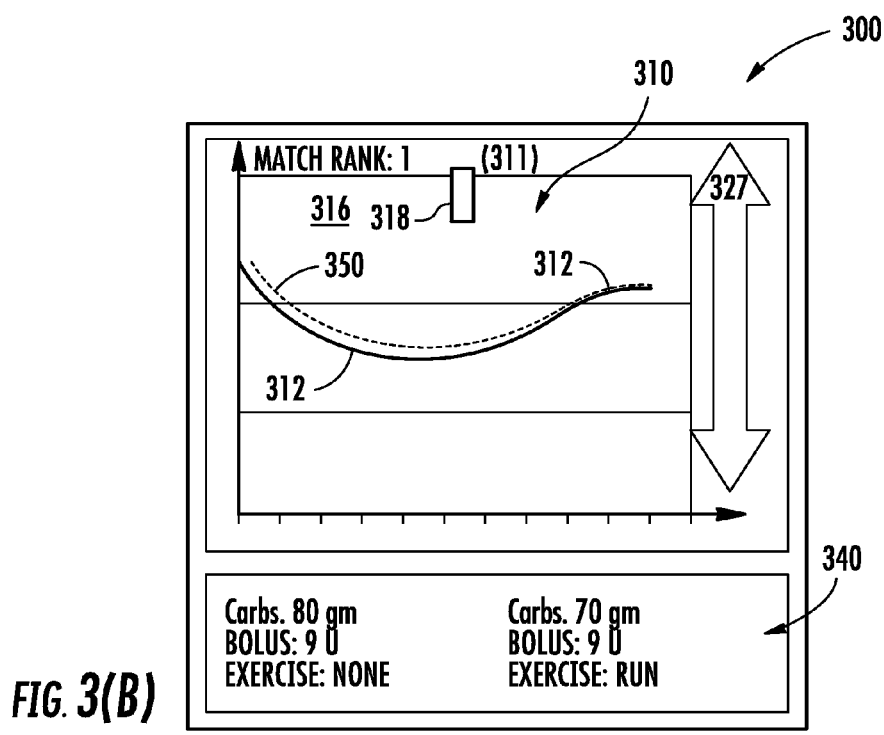
Figure 3C:
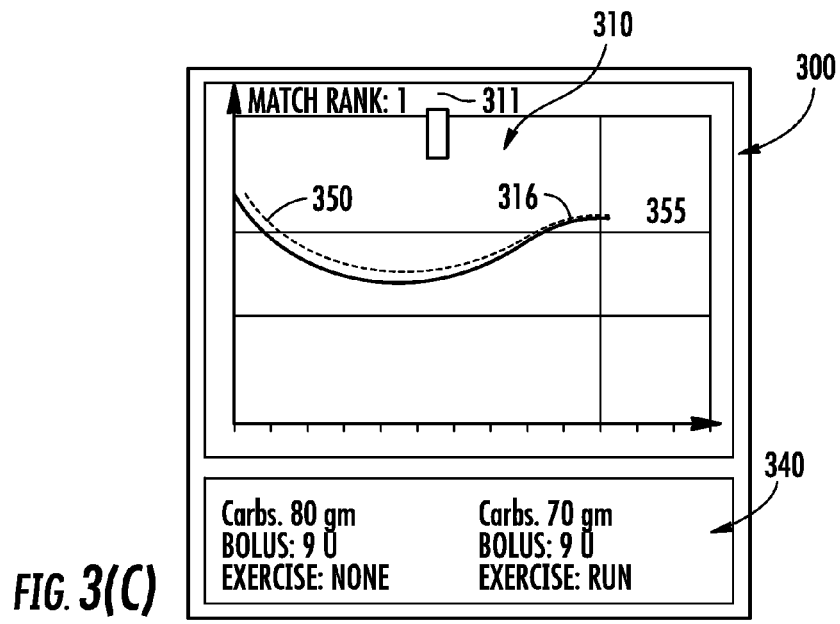
Figure 3D:
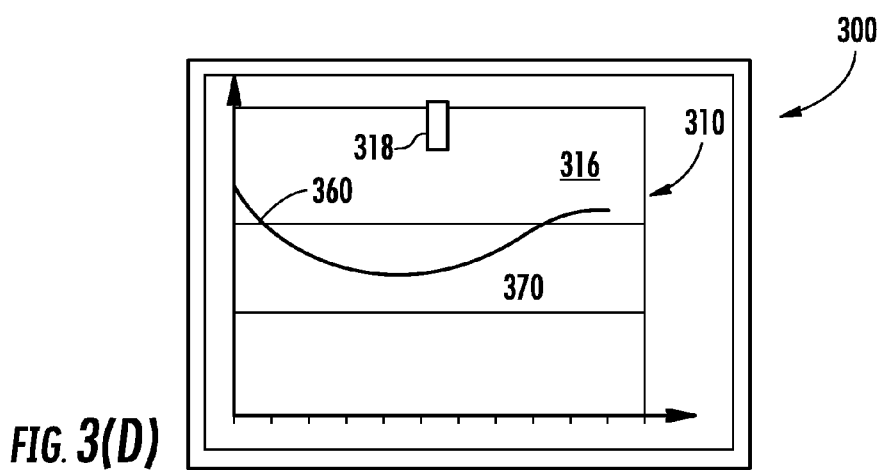

FIG. 3(d) depicts an exemplary display 300 having a raw data plot 360 and a smooth plot 370. Similar to FIG. 3(b), a hypoglycemia region 314, a hyperglycemia region 316, and data tags 318 are shown. The raw data plot 360 comprises raw, noisy data that may be at least one time window data set (or data measurements) from the sensor. The smooth plot 370 displays the compressed version of the raw data from raw data plot 360. The compressed data, which forms a smooth plot 370, may be compressed using the pattern matching or initialization algorithm described herein.

Figure 3E:
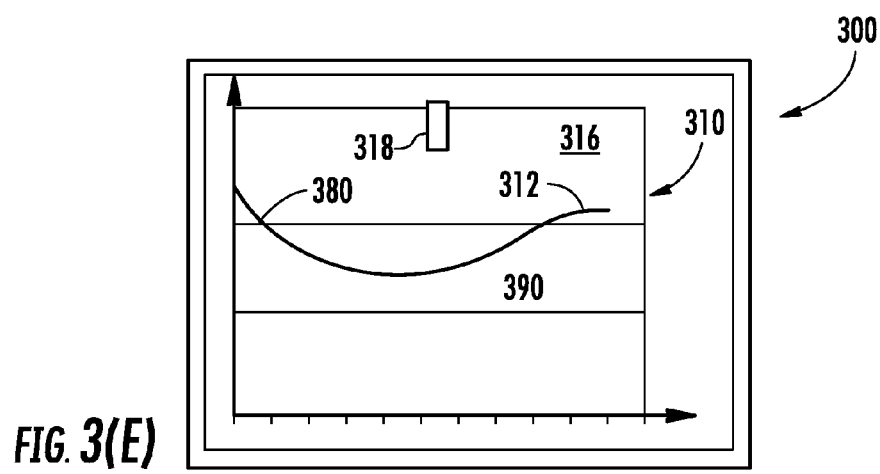

FIG. 3(e) depicts an exemplary display 300 having a reference pattern plot 310. The reference pattern plot 310 includes a plotted reference pattern 312 for data that may be for at least one time window data set (or data measurements) or for results of a query, and multiple pattern match plots 380, 390 plotted on the same axis as plotted reference pattern 312. Similar to FIG. 3(b), a hypoglycemia region 314, a hyperglycemia region 316, and data tags 318 are shown. Of course, other suitable ways in which different components of a pattern match may be depicted will be apparent to those of ordinary skill in the art in view of the teachings herein.

Referring back to FIG. 2, memory 135 may be any type of memory known in the art including, but not limited to, hard disks, magnetic tape, optical disc, semi-conductor memory, a floppy diskette, a CD-ROM, a DVD-ROM, RAM memory, a remote site accessible by any known protocol, or any other memory device for storing algorithms and/or data. In operation, memory 135 may include hardware and software for compressing sensor data to a reduced-rank basis and/or for performing pattern matches, such as e.g., via included analysis logic 132. The analysis logic 132 may be suitably configured to store, interpret and process incoming information and/or to configure the processor 120 to perform such storing, interpreting, and processing of the incoming information, which, e.g., may be the at least one time window data set, raw or transformed, etc. received from the input device 110, the user interface 145, and/or resulting from a query on available data from the input device 110, the database 130, memory 135 and/or external sources via the data interface 115. As will be discussed in greater detail below, the analysis logic 132 may include a pattern-matching algorithm for performing a pattern match of a compressed dataset to past patient data in a reduced-rank space, one or more storage algorithms, one or more data pre-processing algorithm, and/or a initialization algorithm.

Referring to FIG. 2, database 130 may comprise memory capable of receiving and storing the measured and/or detected and/or identified characteristic information, e.g., at least one time window data set, raw data measurements (e.g., numeric values which correspond to a physical measurement), compressed data measurements, transformed data measurements, and may include additional related information, e.g., data tags, pointers, etc. as described above, and/or one or more storage algorithms. When the one or more storage algorithms are executed by the processor 120, it causes the processor 120 to store at least one time window data set, raw data measurements, compressed data measurements, transformed data measurements, a single numeric result calculated or derived from one or more raw data points, etc., in database 130. The processor 120 may also be caused to read at least one time window data set, raw data measurements, compressed data measurements, transformed data measurements, etc. from database 130. The processor 120 may also be caused to index the at least one time window data set, raw data measurements, compressed data measurements, transformed data measurements, etc. from the input device 110 as a function of the time and/or date. The database 130 may collect and receive data measurements automatically via the input device 110 over the window of time, thereby generating and storing the time window data set. The data may be stored in a specialized data structure format for organizing and storing data. Exemplary data structure types may include the array, the file, the record, the table, the tree, etc. The data structure may be designed to organize data to suit a specific purpose so that it can be accessed and worked with.

As noted above, the data structure of database 130 can take on a number of different forms or be structured in a variety of ways. For example, a Kd-tree (K-dimensional tree) may be used. A Kd-tree is a space-partitioning data structure similar to a binary search tree that may be useful for the rapid search and retrieval of multidimensional data. The structure is examined in detail in J. L. Bentley, "Multidimensional divide-and-conquer," *Comm. of the ACM,* 23(4), (April 1980), 214-229 and J. L. Bentley, "Multidimensional Binary Search Trees Used For Associative Searching," *Comm. of the ACM,* 18(9), 1975, which are herein incorporated by reference.

The Kd-tree splits the data having K dimensions at each node using a hyper-plane perpendicular to one of the dimensions. Each internal node has two children, representing a partition along a given dimension of the K-dimensional hyper-plane. Data may be represented in the Kd-tree by their K-dimensional compressed vector and a time parameter that links the compressed vector to a location in the saved raw data. This structure can be used to find: the nearest neighbor to a point or reference pattern, $a_r$, the nearest d neighbors, where d is the number of neighbors of interest, at least one data point within some range r of the reference pattern, $a_r$, where r is the desired distance from the reference pattern. The data structure includes standard methods for performing both n-nearest-neighbor searches and searches for similar data within a specific range that were utilized in this algorithm.

Data may further be stored in database 130 in a queue. In operation, at least one time window data set (or data measurements) received and collected from the input device 110 may be compressed using processor 120 and added to a queue. The queue contains the most recent compressed vectors waiting to be added to the kd-tree. The compressed vectors are moved from the queue to the kd-tree when they are older than N, where N is the length of the current time window. Thus, the compressed vectors are moved to the kd-tree when they are no longer overlapping with the current time window. The time windows are represented in the kd-tree by their k-dimensional compressed vector, any relevant data tags, and a time parameter that links the compressed vector to a location in the saved raw sensor data.

Figure 4:
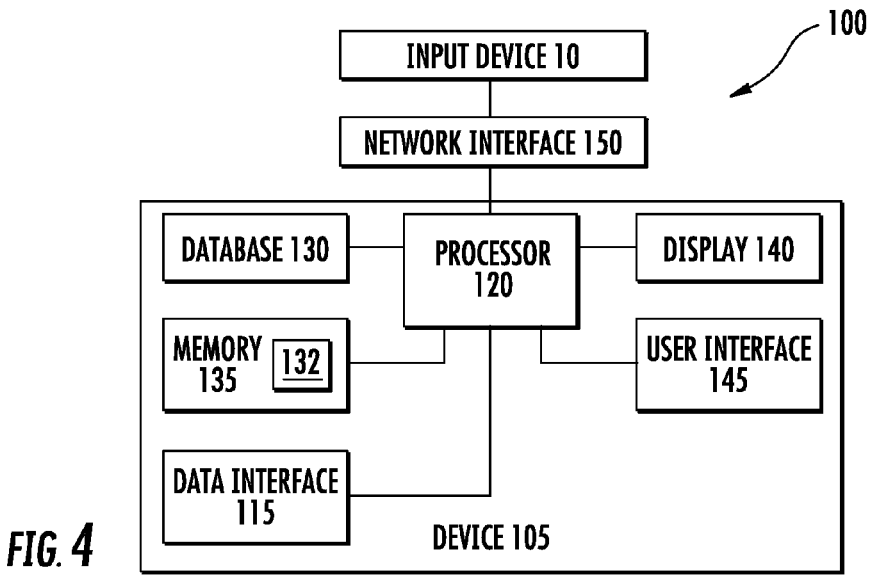
FIG. 4 depicts a block diagram of an exemplary version of a patient monitoring system.

FIG. 4 depicts another exemplary configuration of a patient monitoring system 100, and which hereafter only the difference from the configuration depicted by FIG. 2 are discussed hereafter for purposes of brevity. In this embodiment, the patient monitoring system 100 comprises device 105, input device 110 as a separate component from device 105, and a network interface 150. Device 105 comprises data interface 115, processor 120, database 130, memory 135 along with analysis logic 132, display 140, and user interface 145. The input device 110 is coupled to device 105 via the network interface 150. The network interface 150 may include a wired or wireless connection, and any wired or wireless networking hardware, such as a modem, LAN port, wireless fidelity (Wi-Fi) card, WiMax card, mobile communications hardware, and/or other hardware for communicating with other networks and/or devices. Device 105 may carry out the data storage, pattern matching and display of the results.

Figure 5:
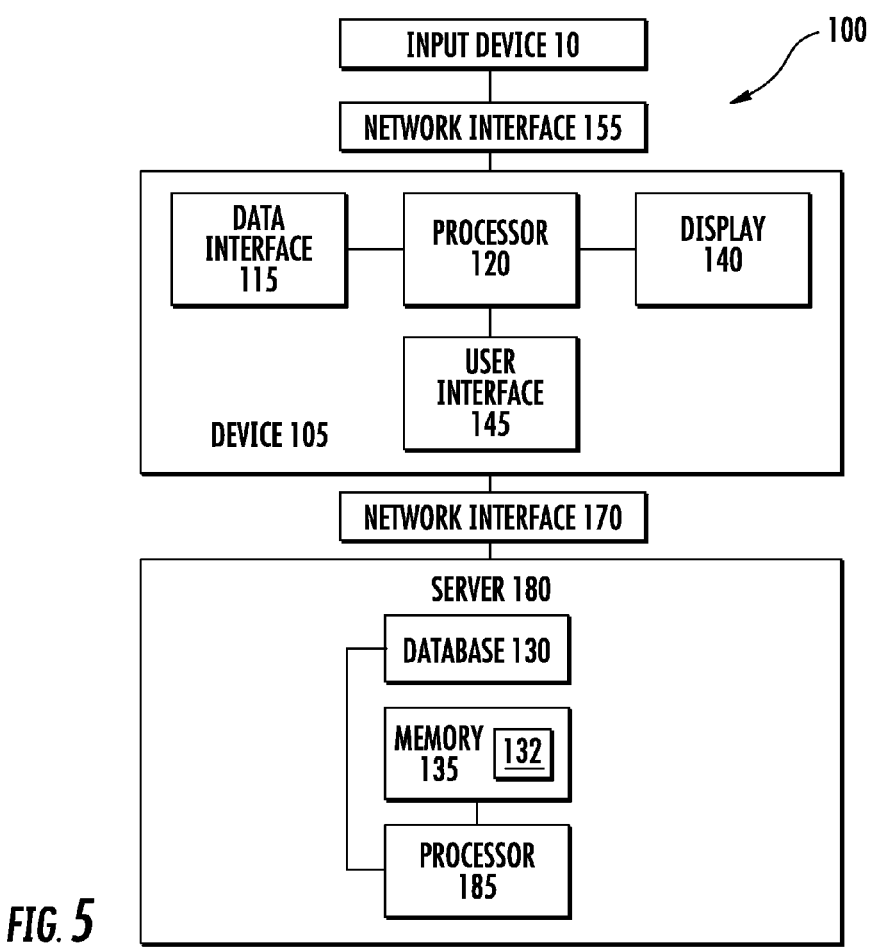
FIG. 5 depicts a block diagram of an exemplary version of a patient monitoring system.

FIG. 5 depicts another exemplary configuration of a patient monitoring system 100, and which hereafter only the difference from the configuration depicted by FIG. 4 are discussed hereafter for purposes of brevity. In this embodiment, the patient monitoring system 100 comprises device 105, the input device 110 as a separate component from device 105, a first network interface 155, a second network interface 170, and a server 180. The input device 110 may provide input to device 105 via the first network interface 155. Device 105 may be coupled to server 180 via a second network interface 170. As noted above with the network interface of FIG. 4, the first and second network interfaces may also include a wired or wireless connection, and any wired or wireless networking hardware for communicating with networks and/or devices. Device 105 comprises data interface 115, processor 120, display 140, and user interface 145. Device 105 may handle data pre-processing, inputting of data request, inputting of data queries, and display of data results. Server 180 comprises the database 130 and memory 135 along with analysis logic 132. In one example, server 180 may also comprise a processor 185 that may be configured to store data measurements into database 130 and perform pattern matching via use of the analysis logic 132.

Figure 6:
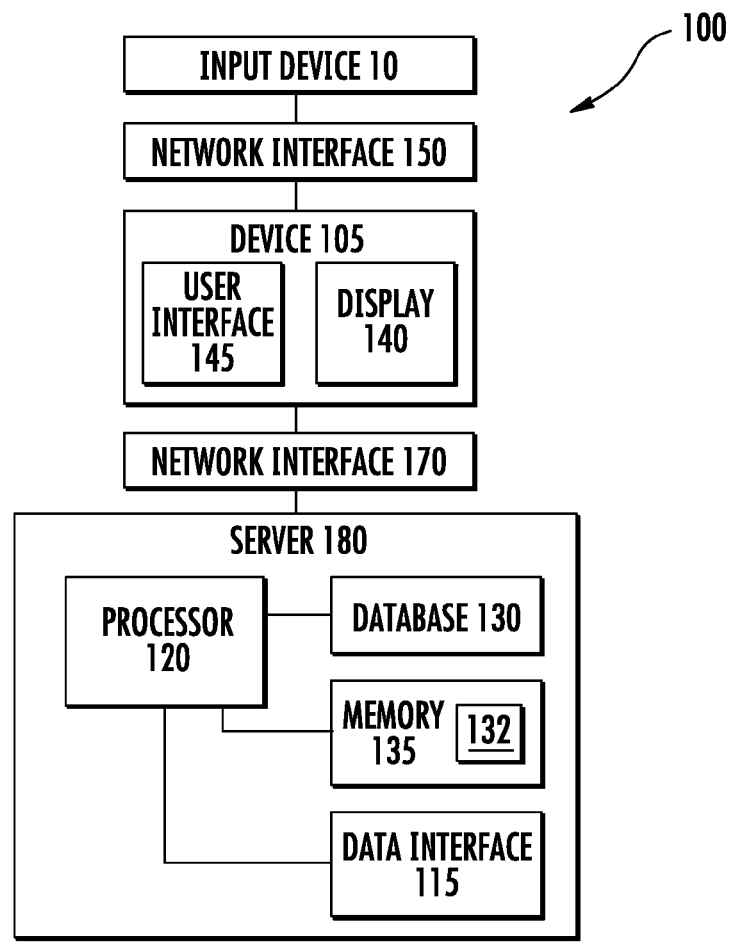
FIG. 6 depicts a block diagram of an exemplary version of a patient monitoring system.

FIG. 6 depicts another exemplary configuration of a patient monitoring system 100, and which hereafter only the difference from the configuration depicted by FIG. 5 are discussed hereafter for purposes of brevity. In this embodiment, the patient monitoring system 100 comprises device 105, input device 110 as a separate component from device 105, a first network interface 155, a second network interface 170, and a server 180. Device 105 comprises a display 140 and user interface 145, and is configured to send raw data to server 180. Server 180 comprises data interface 115, processor 120, database 130, and memory 135 along with analysis logic 132. Server 180 is configured to compress the raw data measurements, store data into database 130 and perform pattern matching.

Figure 7:
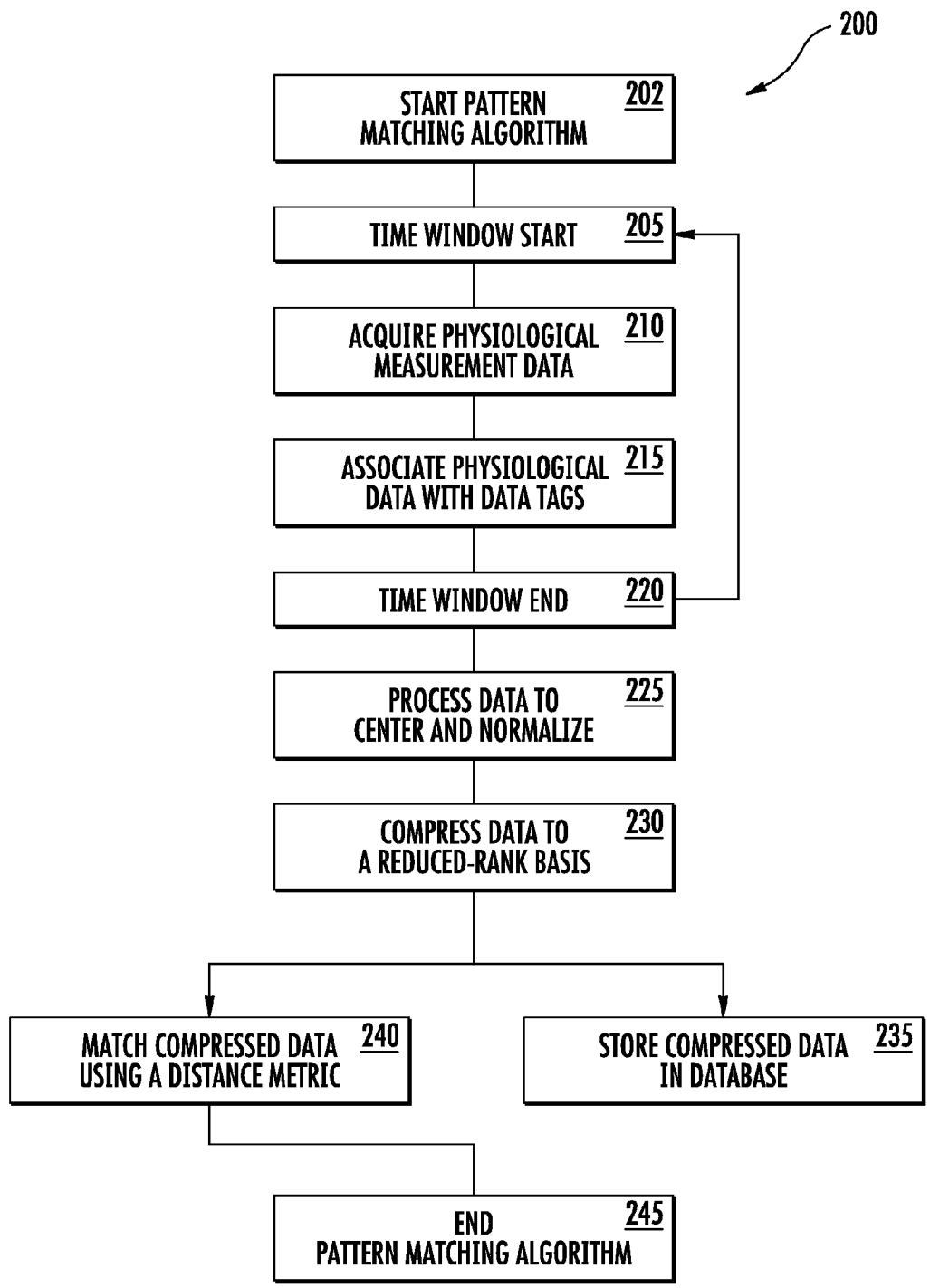
FIG. 7 depicts a flowchart of an exemplary pattern matching process using a patient monitoring system.
Figure 8:
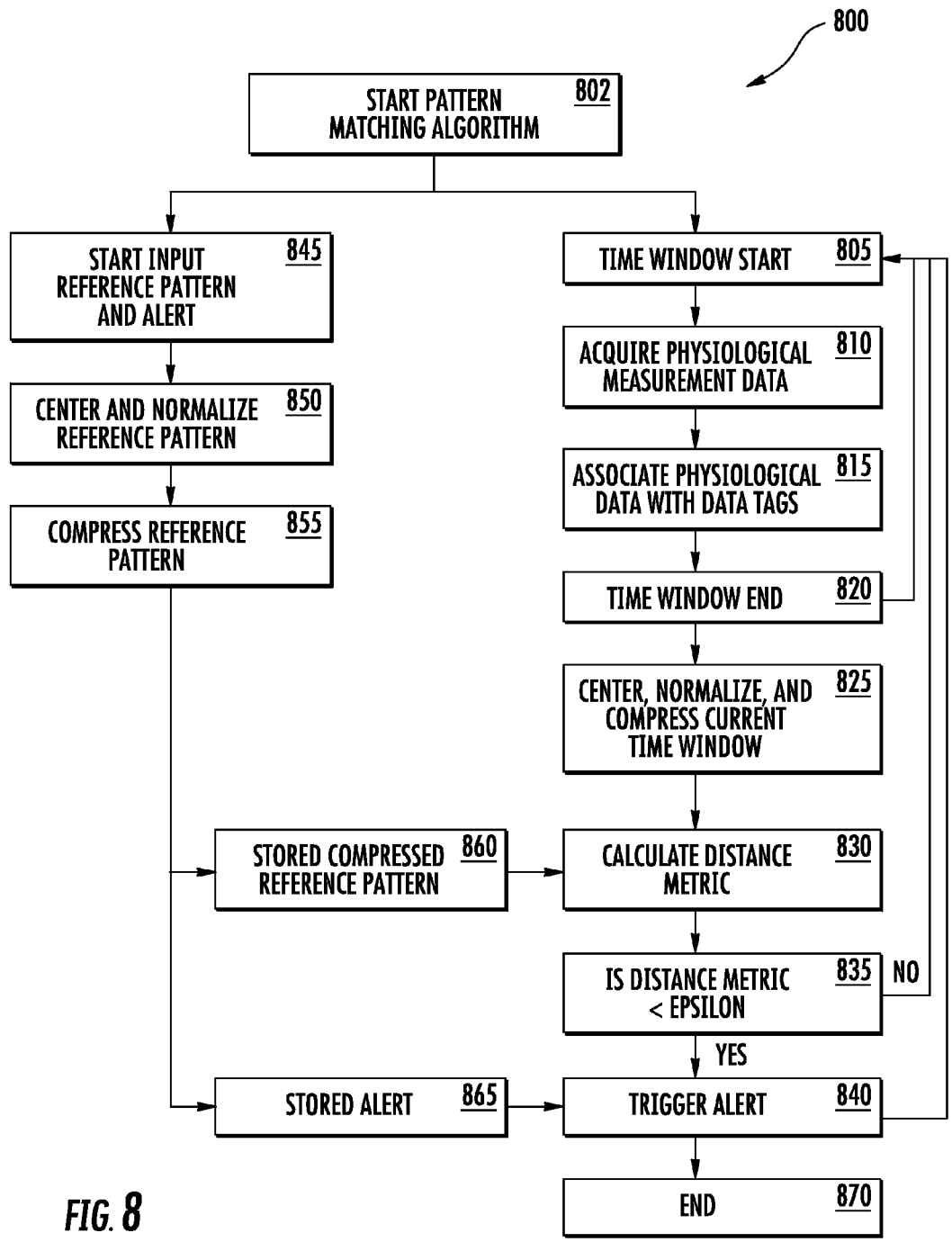
FIG. 8 depicts a flowchart of an exemplary real-time pattern matching process using a patient monitoring system.

FIGS. 7 and 8 depict flowcharts illustrating the general logic of a pattern-matching algorithm 200, 800 for efficiently finding the best match to a reference pattern. FIG. 8 depicts the general logic of a real-time pattern matching algorithm 800 for efficiently identifying a current, or most recent, time window data set that substantially matches the reference pattern. The algorithms 200, 800 are stored in a memory 135, and executed by processor 120 or 185 of the patient monitoring system 100.

Referring to FIGS. 7 & 8, blocks 202, 802 represent the start of the algorithm 200, 800. The input device 110 of a patient monitoring system 100 takes one or more glucose measurements. As noted above, other analyte and/or physiological measurements may also be taken. Blocks 205, 805 represent the start of a time window period for acquiring the one or more glucose and/or physiological measurements. The start of a time window period may be triggered by one or more of the following: user input received via the user interface 145, where the user tells the processor 120 or 185 when a new window is to begin; by a detected or scheduled event; or where a time period has elapsed and a new time period is to automatically begin.

Blocks 210, 810 represent the acquiring physiological measurement data where glucose concentration and/or other physiological data is detected by the input device 110 of the patient monitoring system 100. At least one glucose measurement, physiological measurement, or patient input, received via the user interface 145, is taken during the time window. Alternatively, a plurality of such measurements and patient input may be taken. By way of example only, measurements can be taken in increments of second, minute, hour, day, etc. Each raw data measurement is stored in database 130. Additionally, data may be inputted by the patient 102 using the user interface 145 to answer questions displayed by the processor 120 or 185 on display 140 during the current time window period.

Blocks 215, 815 represent the association of the glucose and/or physiological measurement data with one or more data tags. As mentioned above, the data tags may include when a meal was eaten, when insulin was given, when exercise took place, the amount of nutritional content in a meal, amount of insulin, the amount and/or type of oral medication, what kind of exercise performed, etc. Of course, other data tags that can be associated with the glucose and/or physiological measurement data will be apparent to those of ordinary skill in the art in view of the teachings herein.

Blocks 220, 820 represent the end of the time window period where the processor determines whether the end has been reached. The data from the most recent time window period may be sent to a processor for further processing or alternatively may be sent to the database and held for further processing until two or more time windows of data are available. Then the two or more time windows may be further processed together. As depicted by the arrow, a new time window may be started at the end of the previous time window period, where the process for acquiring glucose and/or physiological measurement data is repeated.

Blocks 225, 825 represents the processing of data to normalize and center the data by the processor to a scale where the distribution of glucose and/or physiological measurements has a mean of zero and standard deviation of one. Blocks 230, 825 represent the compression of raw data to a reduced-rank basis performed by the processor 120. In reduced rank processing, the data may be projected on a set of basis vectors. When glucose and/or physiological measurements are correlated, a small set of basis vectors can explain most of the measurements. The input data is submitted for compression where an Eigen-decomposition is performed on the data to determine the Eigen values and Eigen vectors for the matrix $\hat{X}^T\hat{X}$. The set of K eigenvectors becomes the basis set. This set of K Eigen vectors represents the compressed equivalent of the input data. K is determined using the initialization algorithm, which is further described in FIG. 9.

Figure 9:
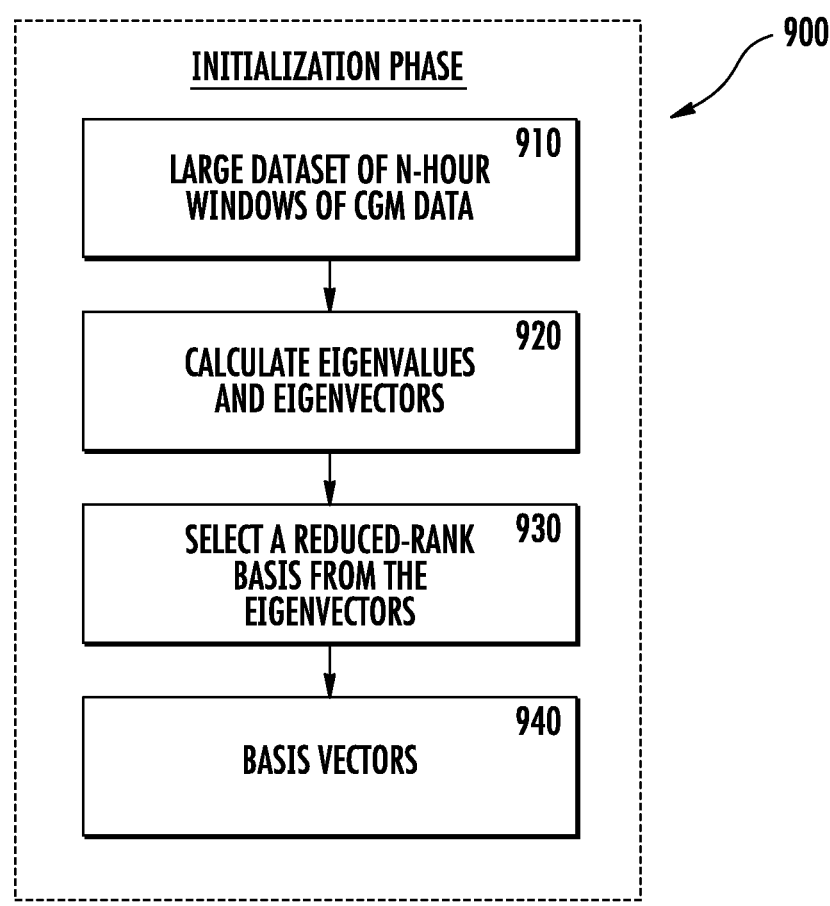
FIG. 9 depicts a flowchart of an initialization algorithm process for compressing data.

FIG. 9 depicts the initialization algorithm 900, which is the process used to find a transformation matrix to convert raw data vectors into compressed reduced-rank vectors. The initiation algorithm may occur one time to find the transformation matrix, and then the transformation matrix may be hard-coded into the pattern-matching algorithm 200, 800 running on the device 105 or system 100. Alternatively, the transformation matrix may be a separate compression algorithm from the pattern-matching algorithm 200, 800. The initiation algorithm may be run on a device separate from the device or system running the pattern-matching algorithm. By way of example only, the initiation algorithm may be run on a PC or other kind of computer.

As depicted, Block 910 represents the step of collecting a large representative sample of time window data sets of a desired length, N (length of a time window data set). The time window data sets may be from a single patient or more than one patient. The data, X, may be from diabetic patients in free-living conditions and may represent a broad range of patient behaviors and results so that it may be representative of a population of diabetic patients. The data, X, may be data from a previous study or may generally come from any large source of glucose measurement data. The data, X, may be centered and normalized, $\hat{X}$, to have a mean of zero and standard deviation of one, and thus may be expressed according to Equation (1) as follows:.

$$\hat{X} = \frac{(X - \bar{x})}{\sigma_x},\quad (1)$$

where X is the M×N matrix of K time window data sets each of length N, $\bar{x}$ is the mean time window data set vector over all K time window data sets, and $\sigma_x$ is the standard deviation time window data set vector over all K time window data sets, K is the length of the compressed reduced-rank vector, and M is the number of sample time window data sets for the initialization algorithm. Data from the time window may be augmented with one or more data tags as discussed above.

Block 920 represents the step of Eigen-decomposition, where the Eigen values and Eigen vectors for the matrix $\hat{X}^T\hat{X}$ is determined, which may be expressed according to Equations (2) and (3) as follows:

$$\lambda = \text{eigenvalues}(\hat{X}^T\hat{X})\quad (2),$$

$$V = \text{eigenvectors}(\hat{X}^T\hat{X})\quad (3).$$

The eigenvectors may be used as the new basis vectors with only the first K vectors, where K is the length of the compressed reduced-rank vector, being used in order to compress the data. The value of K is determined by sorting the Eigen values from largest to smallest, and then calculating the cumulative sum for the sorted list of Eigen values. The Eigen value may be used to show the amount of information explained by its corresponding Eigen vector. The Eigen vectors associated with the smallest Eigen values are removed to compress the data.

Block 930 represents the step of selecting a reduced-rank basis from the Eigen vectors. K may be selected to balance between compressing the data (for algorithm efficiency purposes) and retaining relevant information (level of detail needed in the data). Block 940 represents the step of compressing data into reduced-rank basis vectors. The first K Eigen vectors are used to create a transformation matrix, B, which converts time window data sets to the reduce-rank basis.

A vector is compressed according to Equations (4)-(6) as follows:

$$B = [v_1, v_2, \ldots v_K],\quad (4)$$

$$\bar{x} = \frac{(x_t - \bar{x})}{\sigma_x},\quad (5)$$

$$a_t = B^T \hat{x}_t,\quad (6)$$

where vector $a_t$ represents the reduced-rank version of $x_t$, $x_t$ is the time window data set of length N starting at time t, $B^T$ is the transformation matrix consisting of first K Eigen vectors $[v_1, v_2, \ldots v_K]$, and $v_i$ is the $i^{th}$ Eigen vector that corresponds to $\lambda_i$. The reduced rank vector $a_t$ can be converted back to the original space $\tilde{x}_t$ by multiplying by B, which may be expressed according to Equation (7) as follows:

$$\tilde{x}_t = B\, a_t\quad (7).$$

Data compression may provide, and not limited thereto, the following two noted benefits: it significantly reduces the size of the data for making comparisons, and functions as a filter for removing noise from the signal. Thus, the compression algorithm may match time window data sets with a similar underlying signal rather than matching noise patterns.

Algorithm Initiation Example

Figure 10:
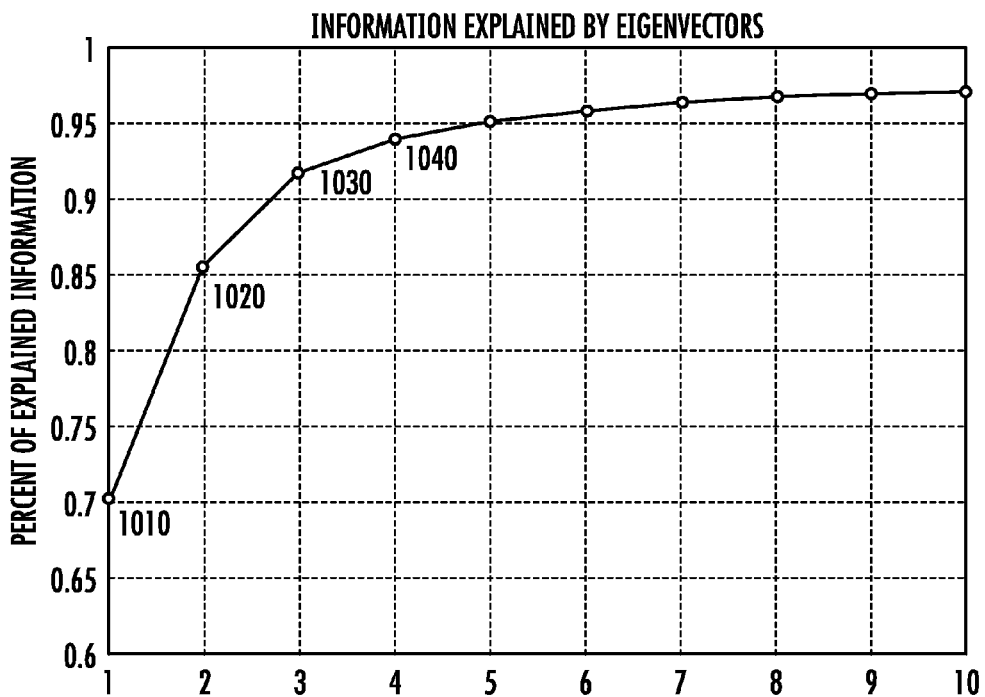
FIG. 10 depicts an exemplary cumulative sum chart of the largest Eigen values.

In some of the experiments performed, the length of each time window data set was four hours. Glucose concentration was measured each minute so each window contained a vector of 240 glucose measurement values. In other experiments performed, the length of each time window data set was two hours. Of course, other time window lengths may be used to collect glucose measurements. In step 1, where a large sample of time window data sets were collected, the length N of each time window data set was 240 minutes, as noted above, and over 100,000 time window data sets were used. The data was centered, normalized, and an Eigen decomposition was performed. The cumulative sum of the Eigen values from the Eigen decomposition was calculated. FIG. 10 depicts an exemplary plot of the cumulative sum of the largest Eigen values divided by the total sum of the Eigen values. The Eigen value may be used to show the amount of information explained by its corresponding Eigen vector. Thus, as shown in the plot on FIG. 10, compressing the time window data sets using the first Eigen vector would retain about 70% of the original data (1010). Using two Eigen vectors would retain about 85% of the original data (1020). Using three Eigen vectors would retain about 91% of the original data (1030). Using four Eigen vectors would retain about 94% of the original data (1040), and so on. In this example, K was selected to be four.

Figure 11:
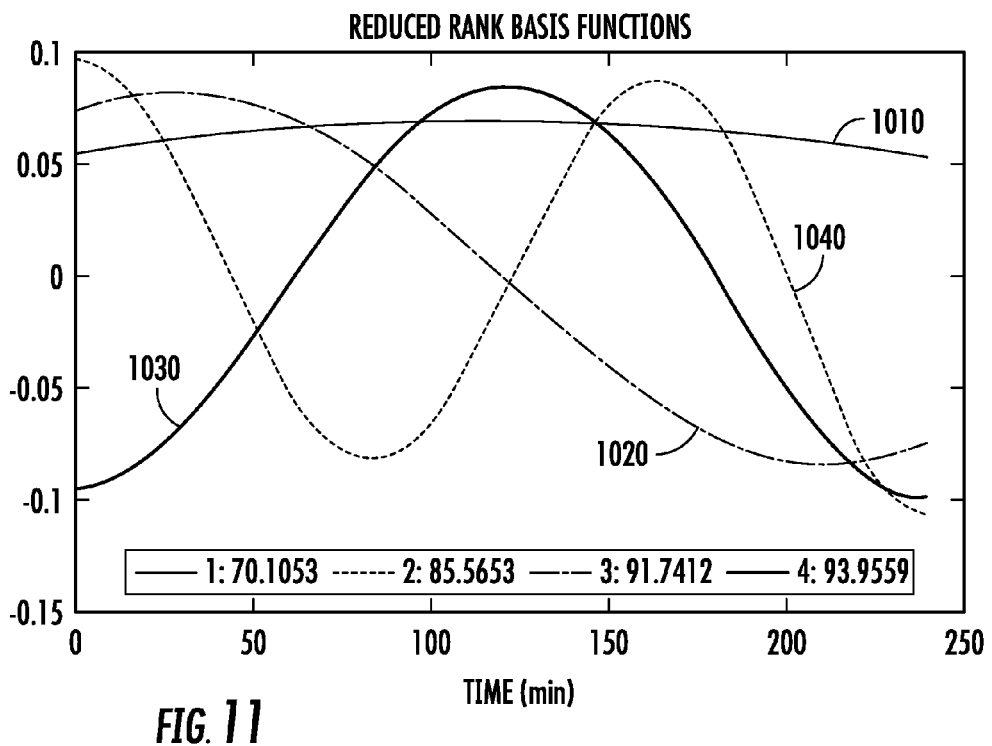
FIG. 11 depicts an exemplary plot of four Eigen vectors.

FIG. 11 depicts a plot of the first four Eigen vectors (1010, 1020, 1030, 1040) calculated using the data from this example, which shows the compressed vectors to be orthogonal. Each vector captures an important type of dynamic found in the raw data. The first Eigen vector 1010 is approximately the mean value of the raw data vector. The second Eigen vector 1020 measures the trend. The third Eigen vector 1030 captures peaks. The fourth Eigen vector 1040 responds to higher frequency components.

Figure 12:
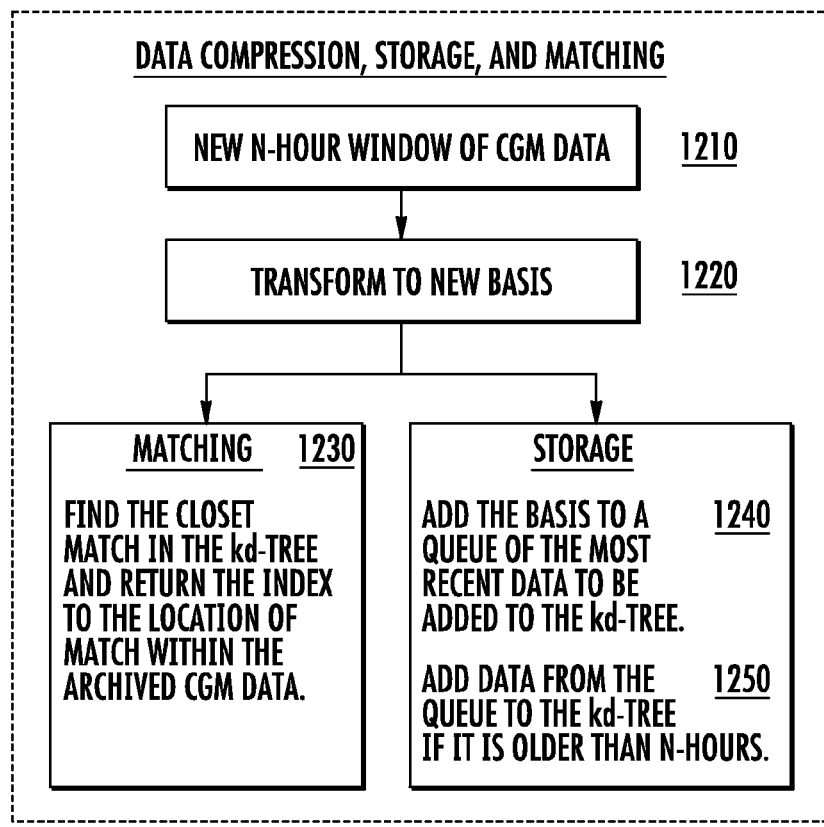
FIG. 12 depicts a flowchart of the match and storage phase of the pattern matching process of FIG. 7.

Referring back to FIG. 7, once the raw data has been compressed, the compressed data may be either pattern-matched by the processor 120 or 185, as represented by block 240, or stored in the database 130 (or alternatively, in memory 135) by the processor 120 or 185, as represented by block 235, both of which are further explained in FIG. 12. Block 245 represents the end of the algorithm.

Referring to FIG. 8, once the raw data has been compressed, the compressed data may be either pattern-matched by the processor 120 or 185, as represented by blocks 830, 835 and 840, or stored in the database 130 (or alternatively, in memory 135) by the processor 120 or 185, both of which are further explained in FIG. 12. Block 870 represents the end of the algorithm.

FIG. 8 also depicts blocks 845, 850, 855, 860, and 865, which generally represent the input and storage of a reference pattern and associated alert to be used during real-time pattern matching. Block 845 represents the input of a reference pattern and/or associated alert into input device 110 using user interface 145.

The reference pattern can be any data set of interest, e.g., historical data (previous day(s), week(s), month(s), year(s), etc.) of the patient 102. The data set can be provided from the input device 110, the database 130, the memory 135, the user interface 145, and/or from any another external source of patient data that the device 105 may communicate with via the data interface 115. It is to be appreciated that as such the reference pattern can be generated from any of the data available to the device 105, and by any method performed by the processor 120, the input device 110 (if provided with processing means), or an external device(s) operating on the data (and provided to the device via the data interface 115), in which to provide a pattern of interest, such as e.g., a glucose curve. Exemplary methods for generating a glucose curve may include: having the processor 120 draw a glucose curve using glucose data measurements provided by the physiological data input device 110, having the processor 120 draw a glucose curve using glucose data measurements read from database 130 and/or memory 135 for the at least one time window or other time periods, having the processor 120 draw a glucose curve using input received via the user interface 145, having the processor 120 select a glucose curve that represents a common behavior or condition (e.g., falling blood glucose during exercise, rise of blood glucose after a meal, etc.) that may be detected in the data of the patient 102, and combinations thereof. In other embodiments, the glucose curve need not be selected from actual glucose data measurements as discussed above in regard to historical and/or external data. The reference pattern can also be generated from data resulting from a query inputted via the user interface 145 and run by the processor 120 on stored data provided in database 130, memory 135 and/or in other external sources that were queried by the processor 120 via data interface 115. The reference pattern may also include any relevant data tags or multi-analyte data, and the generated and/or received reference pattern may be stored in the database 130 and/or memory 135 until needed by the processor 120 for a pattern matching process discussed hereafter in a later section.

The alert is customizable and can be a visual alert, such as a displayed icon or message, or light, an audible alert, such as a beep or music, or a vibrational alert, or a combination thereof. The alert can have single and/or multiple modes of notification. For example, the alert can simultaneously include an audible, visual, and vibrational notification. When an event triggers the alert notification, the user may be notified of the event or condition by feeling the vibration, hearing the audible alert, and/or seeing the visual alert. The alert may be displayed on display 140 of device 105.

In one example, the reference pattern and alert can be used to alert the patient to take specific actions whenever a particular event occurs. For example, the reference pattern can be a post-prandial event, hypoglycemic event, exercise, meals, etc. or any other problematic pattern that has occurred in the patient's past physiological data. Thus, when the event is detected again on a real-time basis, the patient monitoring system 100 will alert the patient to that fact.

Similar to block 825, block 850 represents the processing of the reference pattern to normalize and center the data by the processor to a scale where the distribution of glucose and/or physiological measurements has a mean of zero and standard deviation of one, Block 855 represents the compression of the reference pattern to a reduced-rank basis performed by the processor 120. The processor 120 or 185 may compress the reference pattern and store it for real-time comparison. Block 860 represents the storage of the compressed reference pattern and block 865 represents the storage of the alert in database 130 in a queue or in processor 120 or 185.

Block 830 represents the pattern matching steps which calculate the distance metric between the reference pattern and a real-time (or most current) time window data set. The pattern matching method is further described below in more detail. Block 835 represents the step of determining whether the distance metric is less than a certain value $\epsilon$ which may be set by the user. If the distance metric is less than $\epsilon$, then the alert is activated as shown in block 840. If the distance metric is greater than $\epsilon$, then no alert is activated and the algorithm repeats the process for the next current time window data set. Block 870 represents the end of the pattern matching algorithm 800.

The pattern-matching algorithm 200, 800 may run on any suitable computing device or system, such as device 105, system 100, or provided on a non-transitory computer-readable medium that stores the pattern-matching algorithm 200, 800 in the form of a program providing instructions that when executed by a processor, such as processor 120 or 185, causes the processor to perform the above described acts of blocks 202-245 of FIG. 7 and blocks 802-870 of FIG. 8. The pattern-matching algorithm 200, 800 may be used for efficiently finding the best match or matches to a reference pattern. FIG. 12 further describes the pattern-matching (block 235 of FIG. 7 and blocks 830, 835 and 840 of FIG. 8) and storage phase of the algorithm (block 240 of FIG. 7). Prior to pattern-matching 1230, the current time window data set 1210 is centered and normalized, then transformed into the reduced-rank space 1220 using the transformation matrix, B, that was calculated previously using the initiation algorithm, and which may be expressed according to Equations (8)-(9) as follows:

$$\hat{x}_t = \frac{(x_t - \bar{x})}{\sigma_x}, \tag{8}$$

$$a_t = B^T \hat{x}_t. \tag{9}$$

The closest match or matches may be determined using a distance metric, $j_i$. In one example, the distance metric is the Euclidean distance where the difference in position of two vectors is calculated within the reduced-rank space 1220. Thus, $a_i$ is found by calculating the value that minimizes Equation (10) as follows:

$$j_i = \sqrt{(a_i - a_t)^T (a_i - a_t)} \tag{10},$$

where $a_i$ is the reduced-rank vector of a stored time window data set selected as a potential match, $a_t$ is the reduced-rank reference vector, and T is the transpose function. For real-time pattern matching shown in FIG. 8, the alert is displayed if the value of the distance metric, $j_i$, is less than a threshold value, $\epsilon$. The value for epsilon depends on the distance metric selected, noise penalty, length of time window, etc. In one example, $\epsilon$ is selected to, but can be substantially close to zero. In a general case, $\epsilon$ may be selected using common statistical tests, for e.g., regression analysis, so that the probability that the matches are measurements of the same physiological data is at least 0.95 or in a more stringent case 0.98.

$$j_i \leq \epsilon \tag{11},$$

In another example, the distance metric is the Mahalanobis distance, which also takes into account the correlations of the data set.

$$j_i = \sqrt{(a_i - a_t)^T \Sigma^{-1} (a_i - a_t)} \tag{12},$$

where $\Sigma^{-1}$ is the inverse of the covariance matrix. Of course, other distance metrics may be used to perform pattern matching and will be apparent to those of ordinary skill in the art in view of the teachings herein.

A modified Euclidean distance metric may be used, where the Euclidean distance is modified with an error penalty function to penalize raw data that is too distorted. In one example, the distortion over a raw data window may be estimated by calculating the sum of the absolute error between the compressed data and its raw data, which may be expressed according to Equation (13) as follows:

$$e_i = \Sigma |g_i - \tilde{g}_i|, \text{ where } \tilde{g}_i = B\, a_i \tag{13}$$

where $e_i$ is the sum of the absolute error, $g_i$, is the absolute error of the raw data, and $\tilde{g}_i$ is the absolute error of the compressed data that may be determined to find the closest match or matches that are both close and have less distortion. The closest match or matches may be determined using the Euclidean distance within the reduced-rank space, for example, by calculating the value that minimizes Equation (14) as follows:

$$j_i = \sqrt{(a_i - a_t)^T (a_i - a_t)} + \mu e_i \tag{14}$$

where μ is a parameter used to tune the balance between minimizing the distance and error. This distance metric will tend to find patterns that are both similar and with lower distortion. The value of $j_i$ can be used to evaluate the quality of the match. For example, if $j_i$ is less than some threshold then the match could be qualitatively described as "excellent," "good," or "poor." The distance metric may include components representing the difference between tags associated with the data.

$$e_{tag} = f(k_i, k_t) \tag{15}$$

In operation, when the pattern-matching algorithm 200 is executed by a processor, e.g., processor 120 or 185, it can cause the processor to further perform the pattern match by determine the distance metric between the nearest neighbor and the reference pattern. In another example, when the pattern-matching algorithm 200 is executed by the processor 120 or 185, it can cause the processor to further perform the pattern match by determine the distance metric between the nearest d neighbors and the reference pattern. In another example, when the pattern match algorithm is executed by a processor, e.g., processor 120 or 185, it can cause the processor to further perform the pattern match by determine the distance metric between at least one data point within some range r of the reference pattern, where r is the desired distance from the reference pattern. Pattern-matching algorithm 800, when executed by a processor 120 or 185, it can cause the processor to pattern-match using the most recent or current time window data set and the reference pattern. When the most recent or current time window data set matches the reference pattern, the device 105 triggers an alert, which can include the display of an alert message containing therapy information.

The pattern-matching algorithm 200, 800 may be run on, for example, a continuous glucose monitor system or other patient monitoring systems as described above. The pattern-matching algorithm 200, 800 may also be run on other exemplary continuous glucose monitors manufactured by, for example, Medtronic, DexCom, and Abbott Diabetes Care or any other system that may be used to display and/or analyze raw data from a physiological sensor, and/or reference patterns from actual or generated data, for patterns.

In one example, a patient monitoring system runs a pattern matching algorithm. The patient monitoring system comprises an input device which receives a biological sample and acquires a plurality of physiological measurements of a patient within a time window thereby generating at least one time window data set, a memory storing a pattern matching algorithm, a database to store the at least one time window data set, and a processor in communication with said input device to receive said generated at least one time window data set and in communication with the memory in order to execute the pattern matching algorithm. When the pattern matching algorithm is executed by the processor, it causes the processor to compress the at least one time window data set into a reduced-rank space and perform a pattern match between a reference pattern and the stored at least one time window data set using a distance metric. The memory may further store a data pre-processing algorithm. The data pre-processing program, when executed by said processor, may cause said processor to normalize and center the at least one time window data set to a scale where the distribution of the plurality of physiological measurements has a mean of zero and a standard deviation of one.

The generated at least one time window data set may be compressed into a reduced-rank space using a transformation matrix. The transformation matrix may be determined by an initialization algorithm, which when executed by the processor, causes the processor to perform an Eigen-decomposition on a large, representative physiological measurement dataset to determine λ eigenvalues and V eigenvectors, calculate the cumulative sum of the eigenvalues, and select a subset K of the largest Eigen vectors. By way of example only, K can be six or less. In another example, K can be five or less. In another example, K can be four or less. By way of example only, K may also be preselected to retain up to about 90% of the original data from the at least one time window data set. In another example, K may be preselected to retain up to about 95% of the original data from the at least one time window data set. In another example, K may be preselected to retain up to about 98% of the original data from the at least one time window data set.

When the pattern matching algorithm is executed by said processor, it may cause the processor to pattern match by determining the distance metric within the reduced-rank space. It may also cause the processor to pattern match by determining the closest match that calculates the value that minimizes the distance metric within the reduced-rank space. The pattern matching algorithm, when executed by said processor, may further cause the processor to determine the absolute error of a pattern match using the distance metric within the reduced-rank space or of the closest match that minimizes the distance metric within the reduced-rank space. The processor may perform the pattern match using a Kd-tree search or a naïve exhaustive search.

The patient monitoring system may further comprise a database and one or more storage algorithms. When the one or more storage algorithms are executed by said processor, it may cause the processor to store a compressed dataset in a Kd-tree structure in the database. It may also cause the processor to add the compressed dataset to a queue, and then add the compressed dataset from the queue to the Kd-tree structure. By way of example only, data sets may be stored in the database at a regular interval, based on an event, based on a data tag, based on the pattern of the data, or when requested by the user.

In another example, a patient monitoring comprising a sensor and a processor may use the pattern-matching algorithm for processing at least one time window data set. In operation, the patient monitoring automatically receives via the sensor a biological sample into the patient monitoring, acquires a plurality of physiological measurements automatically generates at least one time window data set, and automatically has the processor process the generated at least one time window data set to normalize and center the at least one time window data set to a scale where the distribution of physiological measurements has a mean of zero and a standard deviation of one, compress the normalized at least one time window data set into a reduced-rank space, and perform a pattern match between a reference pattern and the compressed at least one time window data set using a distance metric within a reduced-rank space.

During the pattern match, the processor may automatically find the closest match by calculating the smallest distance metric value between the reference pattern and one of the stored at least one time window data set (i.e., potential match) to find the closest match within the reduced-rank space. This may be done by performing a Kd-tree search or by performing a naïve exhaustive search. The processor may also automatically finds the absolute error of the pattern match or closest match.

The processor may automatically compress the generated or normalized dataset into a reduced-rank space by performing an eigen-decomposition via decomposing an $\tilde{X}^T\hat{X}$ matrix into $\lambda$ eigenvalues and V eigenvectors. Then the processor may automatically calculate the cumulative sum of the eigenvalues, determine the corresponding eigenvector for each eigenvector, and select a subset of eigenvectors by balancing between data compression and preservation of relevant information. the may occur by automatically applying an orthogonal transform matrix to said subset of eigenvectors to provide a compressed reduced-rank vector. The processor may also automatically store the compressed dataset in a Kd-tree.

In another example, a non-transitory computer-readable medium may store the pattern matching algorithm in the form of a program. When the program is executed by a processor, it causes the processor to perform at least a pattern match of a reference pattern to a stored data time window data set collected via a patient monitoring system using a distance metric. The program may cause the processor to perform the pattern match by finding the nearest neighbor to the reference pattern. In another example, the program causes the processor to perform the pattern match by finding the nearest d neighbors, where d is the number of neighbors of interest. In a further example, the program causes the processor to perform the pattern match by finding at least one data point within some range r of the reference pattern, where r is the desired distance from the reference pattern. The program may cause the processor to further perform the pattern match by determine the absolute error between the nearest neighbor and the reference pattern, between the nearest d neighbors and the reference pattern, and/or between the at least one data point within some range r of the reference pattern, where r is the desired distance from the reference pattern.

As noted above, when running a pattern matching algorithm, the reference pattern can be the most recent at least one time window data set (except for where a real-time pattern matching algorithm is running) and/or can be any other pattern of interest, e.g., a diabetes patient's past data, another source of glucose data, a generated glucose curve, etc. Exemplary methods for generating a glucose curve may include: drawing a glucose curve using, for example, a mouse, a keyboard, a touch screen, etc., selecting a glucose curve that represents a common behavior or condition (e.g., falling blood glucose during exercise, rise of blood glucose after a meal, etc.), etc. The glucose curve need not be selected from actual glucose data measurements, but can be selected from actual glucose measurement data. The reference pattern may also include relevant data tags.

The pattern matching algorithm can be used in a variety of ways. For example, pattern matching can be performed to identify problematic meals. At times, diabetic patients are face with the challenge of controlling post-prandial (i.e., after a meal) hyperglycemic excursions. Diabetic patients can monitor their post-prandial glucose behavior by glucose testing at a distinct time after a prandial event. This, however, may neglect the dynamics of the glucose excursion, that is, the change in glucose or other relevant data (e.g., carbohydrate intake, other meal information, insulin levels, etc.) after a meal. The pattern matching algorithm may be used by a diabetic patient or health care provider to draw quickly a reference pattern of the hyperglycemic post-prandial event that corresponds to the dynamics of the meals a patient has consumed. Finding patterns in the patient system that are similar to the reference pattern may allow for identification of problematic meal events. A health care provider or diabetic patient may correct these events in the future by more accurately estimating the carbohydrate content or modifying treatment appropriately. The pattern matching algorithm may also be used to identify multiple instances where hyperglycemia was most severe and determine patterns that may have caused these deviations. The pattern matching may be used to identify similar meals. A search of past data may be made for similar glucose patterns and/or behavioral patterns to assist a diabetic patient to recollect past decisions and outcomes. In operation, a user may draw or select a pattern, and the system calculates the percentage of time that a diabetic patient's closest match data is similar to the reference pattern within certain boundaries.

In another example, pattern matching can be performed to identify hypoglycemic events. Diabetic patients are also sometimes faced with undetected nocturnal hypoglycemic episodes. Undetected hypoglycemic episodes are possible on account of both meal-influenced glucose-insulin dynamics and physical activity. A reference pattern may be used by a user to identify periods where the patient experienced hypoglycemia to analyze these episodes to provide a framework for identifying hypoglycemia causes and providing solutions. For example, the combination of closest match patterns and meal, insulin, and physical activity information may serve as a useful tool in analyzing patient hypoglycemic behavior. It may also indicate strategies to avoid hypoglycemia. In operation, a user may draw or select a pattern, and the system calculates the percentage of time that the diabetic patient's closest match data is similar to the reference pattern within certain boundaries.

In another example, pattern matching can be performed to estimate proactively bolus or meal intake. A reference pattern and meal information may be used by a user to search through a meal database and observe past glycemic behavior. The user may then analyze post-prandial behavior based on the past event, and make insulin bolus changes to avoid a post-prandial hyperglycemic excursion. Similarly, a user can use past physical activity, insulin and meal information to correct for impending hypoglycemic episodes before exercising or other physical activity.

In another example, pattern matching may be used in a real-time patient monitoring system (running the real-time pattern matching algorithm) to notify a patient if a most recent or current time window data set is substantially similar to a reference pattern. The reference pattern is input into the device along with an alert that will display when the monitoring system identifies a most recent or current time window data set that is substantially similar to the reference pattern. When the most recent or current time window data set matches the reference pattern, an alert will be triggered. The reference pattern can be any problematic pattern in the patient's physiological data (e.g., post-prandial behavior, hypoglycemic events, hyperglycemic events, exercise, etc.)

Referring to FIG. 12, during the storage phase, data that is available and compressed may be added to a queue 1240. The queue contains the most recent compressed vectors waiting to be added to the kd-tree. The compressed vectors are moved from the queue to the kd-tree when they are older than N, where N is the length of the current time window 1250. Thus, the compressed vectors are moved to the kd-tree when they are no longer overlapping with the current time window. The time windows are represented in the kd-tree by their k-dimensional compressed vector and a time parameter that links the compressed vector to a location in the saved raw data.

Pattern Match Examples

Exemplary pattern match results were generated by finding the closest match in a database containing 138,489 stored four-hour data windows compressed into 4-dimensional vectors. For each time window, the closest match was found in the reduced-rank space. The searches were performed using a naïve exhaustive search and the efficient kd-tree search. Details of the exemplary pattern match results will be discussed in more detail below using FIGS. 13(a) and 13(b), 14(a) and 14(b), 15(a)-15(c), 16(a)-16(e) and 17.

Figure 13A:
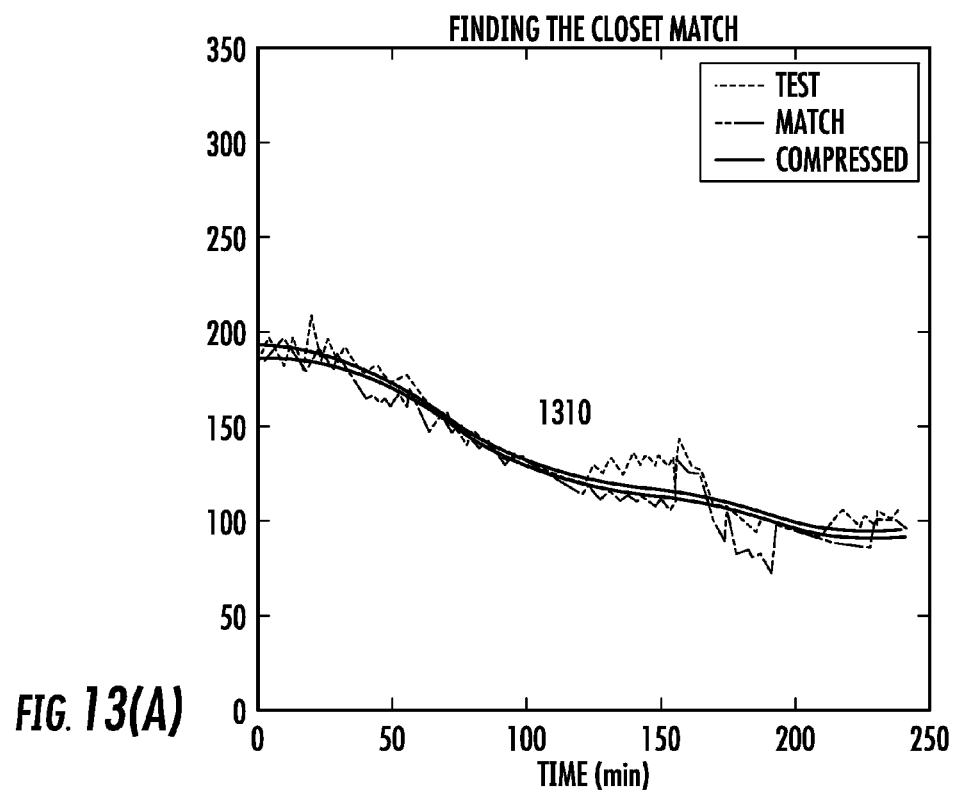
FIGS. 13(a) and 13(b) depict exemplary pattern match plots having a downward trend.
Figure 13B:
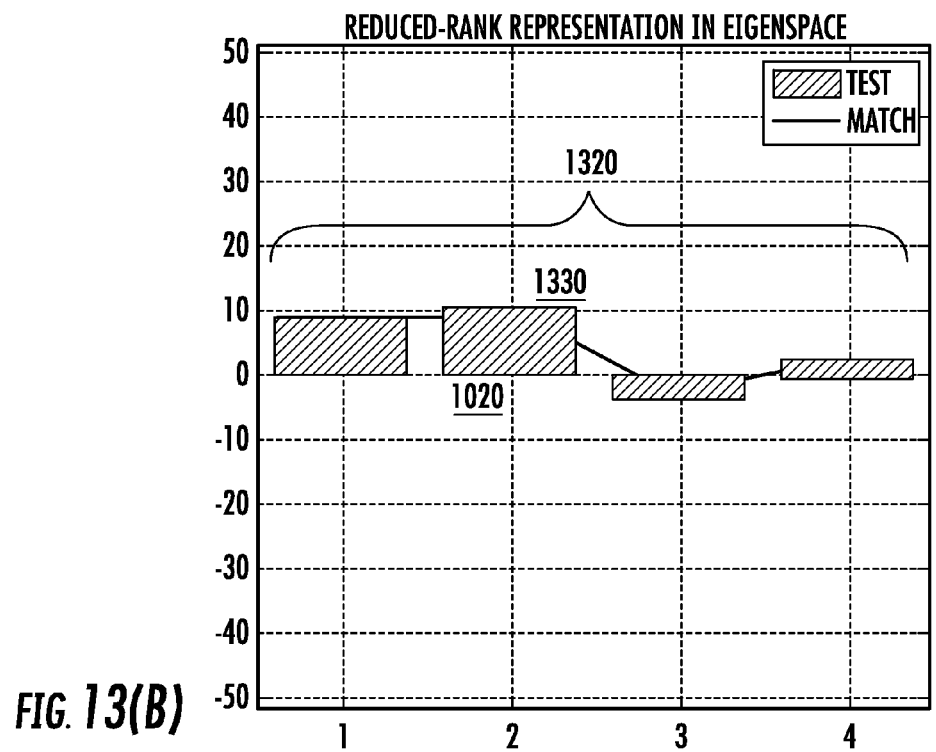
Figure 14A:
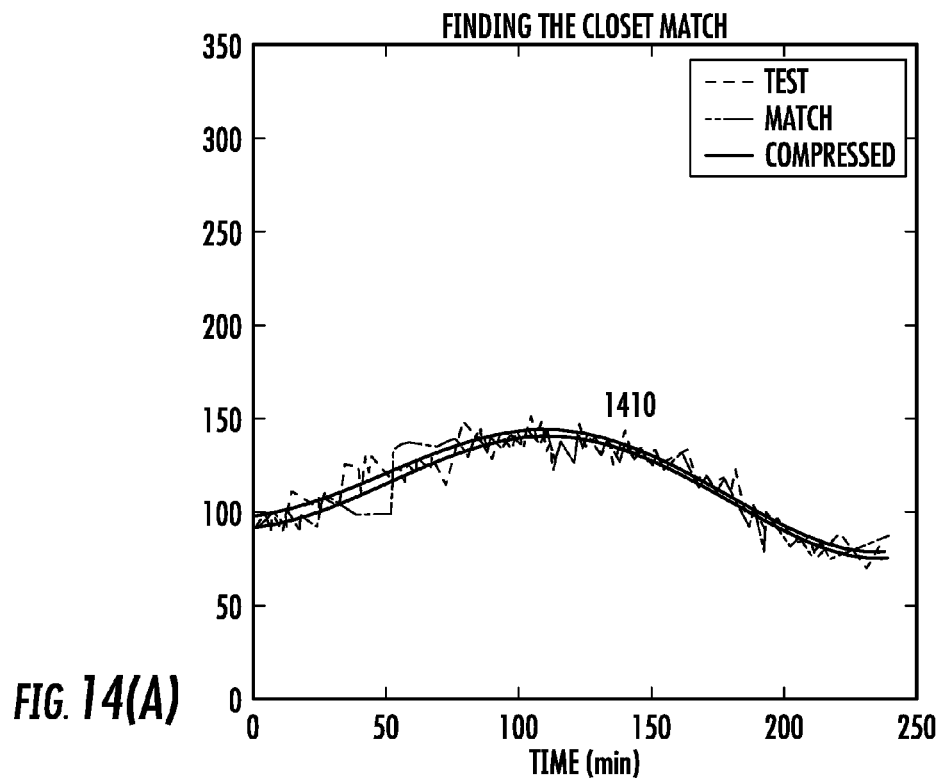
FIGS. 14(a) and 14(b) depict exemplary pattern match plots having a peak.
Figure 14B:
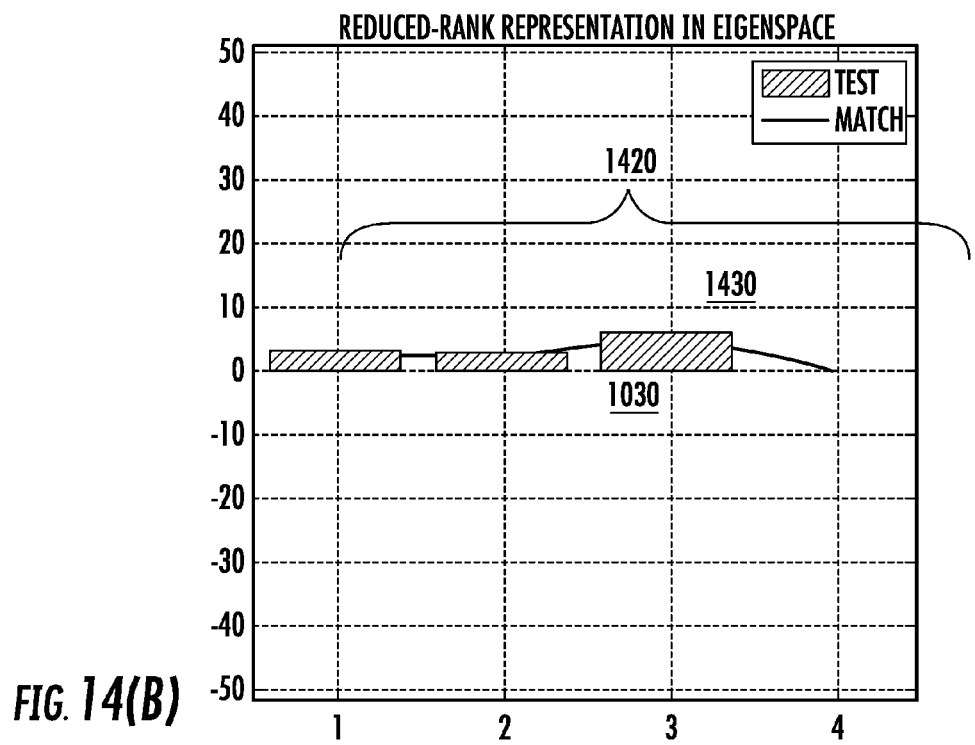

FIGS. 13(a), 13(b), 14(a) and 14(b) depict two results from an exemplary pattern-match search for the closest match. FIGS. 13(a) and 14(a) show exemplary plots (1310, 1410) of the time window raw data used for the pattern-match search, its compressed version, and the raw data of a match along with its compressed version. FIGS. 13(b) and 14(b) show exemplary plots of the value of the compressed vectors with the time window data plotted as bars (1330, 1430) and the match as a line (1320, 1420). The exemplary plots of FIGS. 13(a) and 13(b) show a downward trend so the second Eigen vector 1020 contains the strongest response. The exemplary plots of FIGS. 14(a) and 14(b) show a peak so the third Eigen vector 1030 contains the strongest response. The ability to interpret the values in the reduced-rank space could be used for other algorithms, such as hypoglycemia prediction, meal pattern classification, and noise-filtering.

Figure 15A:
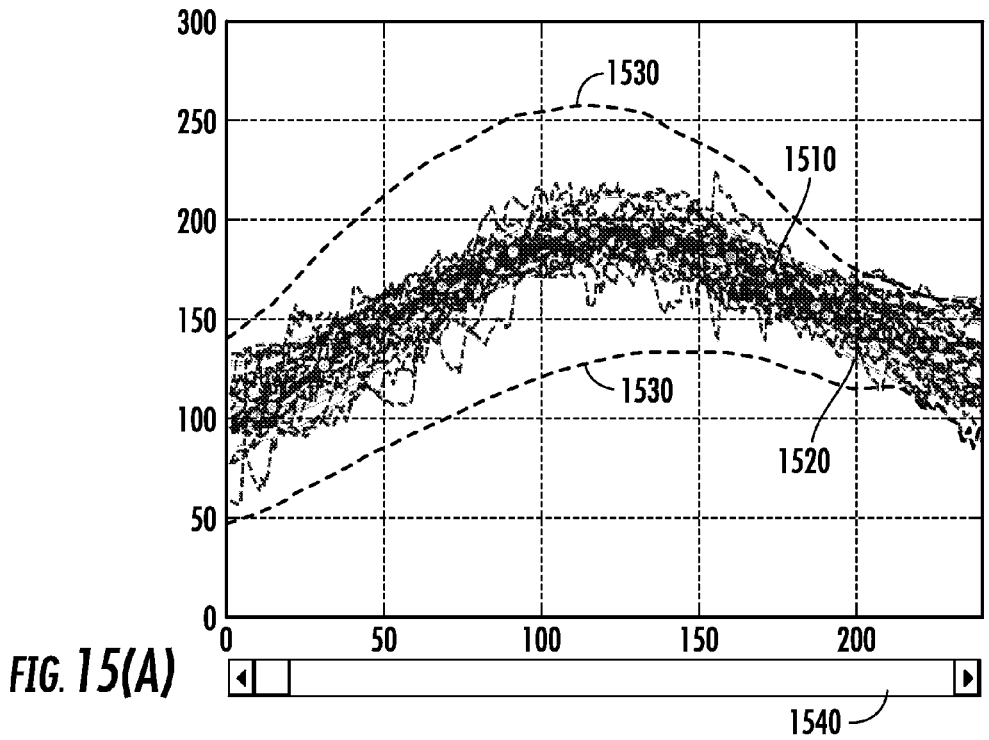
FIGS. 15(a)-15(c) depict exemplary displays of pattern match plots over a 4 hour time period.

FIG. 15(a) depicts an exemplary display of a reference pattern plot of blood glucose concentration over time. In this example, a four hour reference pattern 1510 (shown as a line with circle points) was drawn and the pattern matching algorithm returned the reduced rank vectors of the top 20 matches 1520 shown as smooth lines. The noisy lines are the top 20 matches shown as raw data vectors. The top 20 matches 1520 were determined using Euclidean distance in the reduced-rank space and the sum of absolute error between the potential match's raw data vector and its reduced-rank vector. As depicted, the plot contains the reference pattern 1510 and all 20 matches 1520. Alternatively, the plot may contain the reference pattern and one or more matches. The plot may also contain error boundaries 1530 that range from about +/−15% to +/−50%. The error boundaries 1530 may be useful for showing a visual comparison. Also, shown is a scroll bar 1540 at the bottom of the screen that may be used to scroll through and/or select a specific match. The scroll bar 1540 may be a touch sensitive display, whereby the scroll bar on the screen is touched with a finger and then moving the finger in a desired direction on the screen. The arrows to the left and right of scroll bar 1540 may be touched with a finger on the screen to scroll through and/or select a specific match. In addition, a mouse may also be used to scroll through using scroll bar 1540 or the left and right arrows. As a specific match is selected, the display changes to highlight the specific match. Matches that are not selected may be dimmed and placed in the background.

Figure 15B:
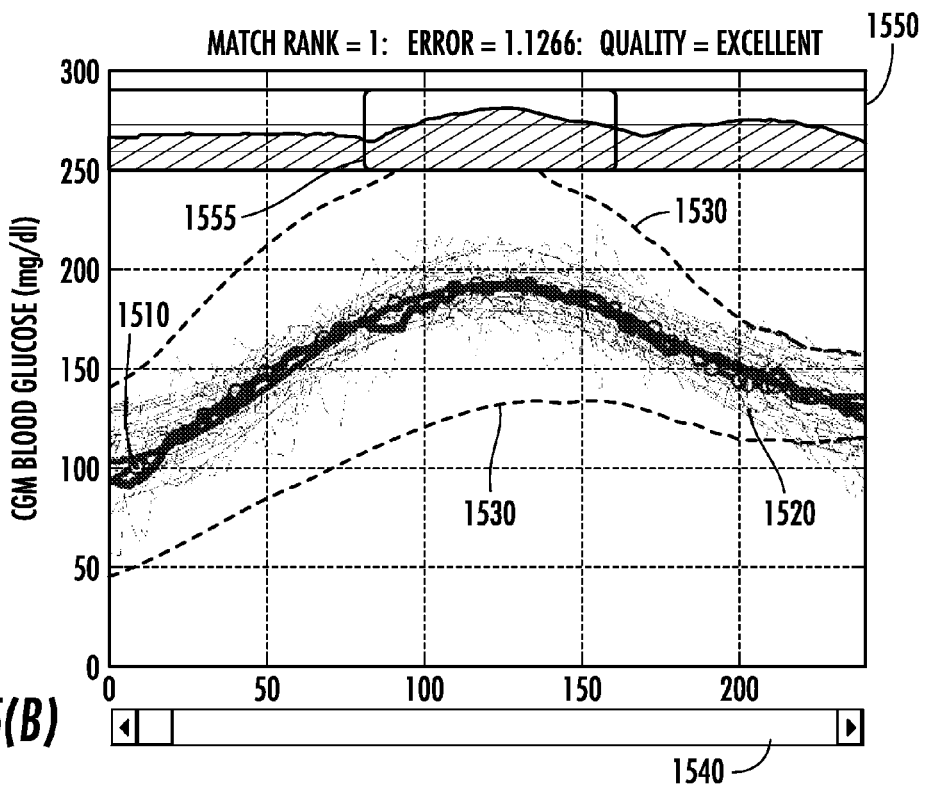

FIG. 15(b) depicts an exemplary display of a reference pattern plot of blood glucose concentration over time. Similar to FIG. 15(a), the plot contains the four hour reference pattern 1510 (shown as a line with circle points), reduced rank vectors of all 20 matches 1520 (shown as smooth lines), raw data vectors of all 20 matches (shown as noisy lines), error boundaries 1530 and scroll bar 1540. Also depicted are two highlighted lines showing the reduced rank vector of a particular match and the corresponding raw data vector (which is the noisy highlighted line) for the match. The display also includes a match rank, which ranks the matches in order from closest to Nth closest match, where N is the number of matches. In this particular example, the match rank can range from 1 to 20. FIG. 15(b) shows a match rank of 1 indicating that the highlighted match is the closest match to the reference pattern. The other matches are dimmed and placed in the background. Also depicted is a match error, which shows the absolute error between the match and the reference pattern. The quality assessment label is also depicted and is based on the match error numbers. A quality assessment label may comprise excellent, good, fair, poor, bad, awful, etc. or other label may be used to indicate the quality of a match. The display includes a timeline 1550 at the top of the graph, which depicts the matched section 1555 placed in a timeline that may provide context of the match.

Figure 15C:
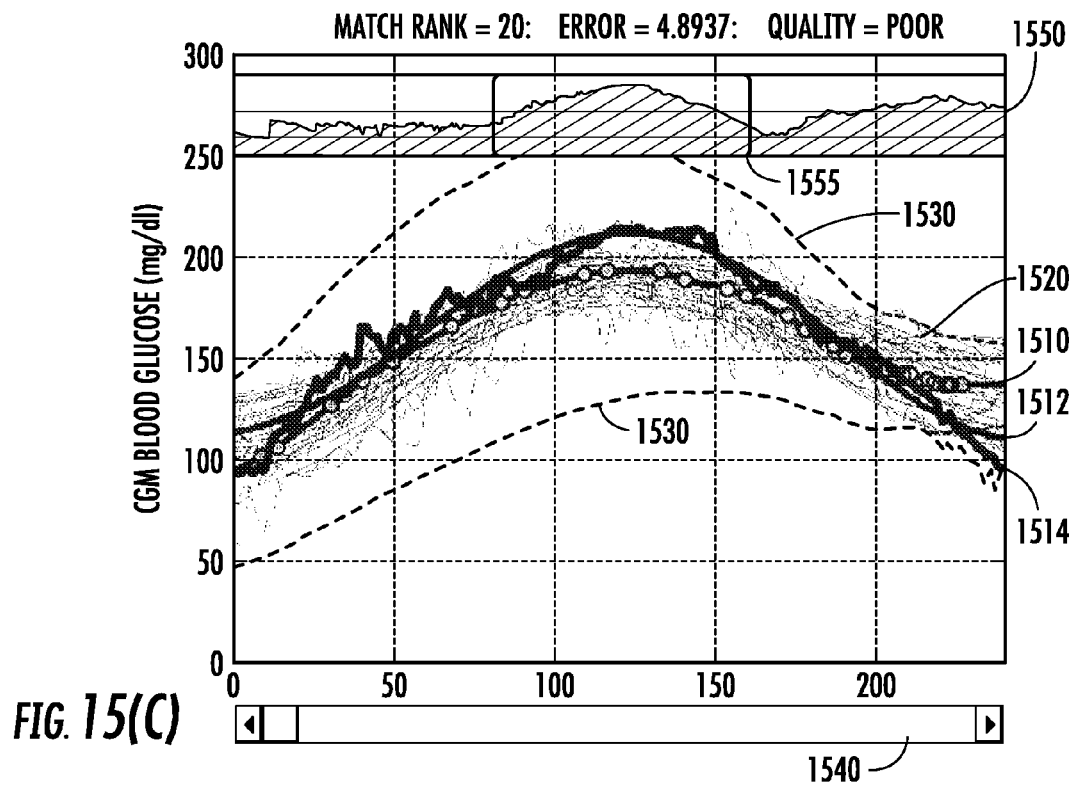

FIG. 15(c) depicts another exemplary display of a reference pattern plot of blood glucose concentration over time. Similar to FIGS. 15(a) & 15(b), the plot contains the four hour reference pattern 1510 (shown as a line with circle points), reduced rank vectors of all 20 matches 1520 (shown as smooth lines), raw data vectors of all 20 matches (shown as noisy lines), error boundaries 1530 and scroll bar 1540. Also depicted are two highlighted lines showing the reduced rank vector of a particular match 1512 and the corresponding raw data vector 1514 (which is the noisy highlighted line) for the match. FIG. 15(c) depicts a match rank of 20 indicating that the highlighted match is the 20th closest match to the reference pattern. The other matches are dimmed and placed in the background. Also depicted is the match error and quality assessment label. The display in this example shows a high match error and therefore, the quality assessment label is poor. The display also depicts a timeline 1550 at the top of the graph showing the matched section 1555.

Figure 16A:
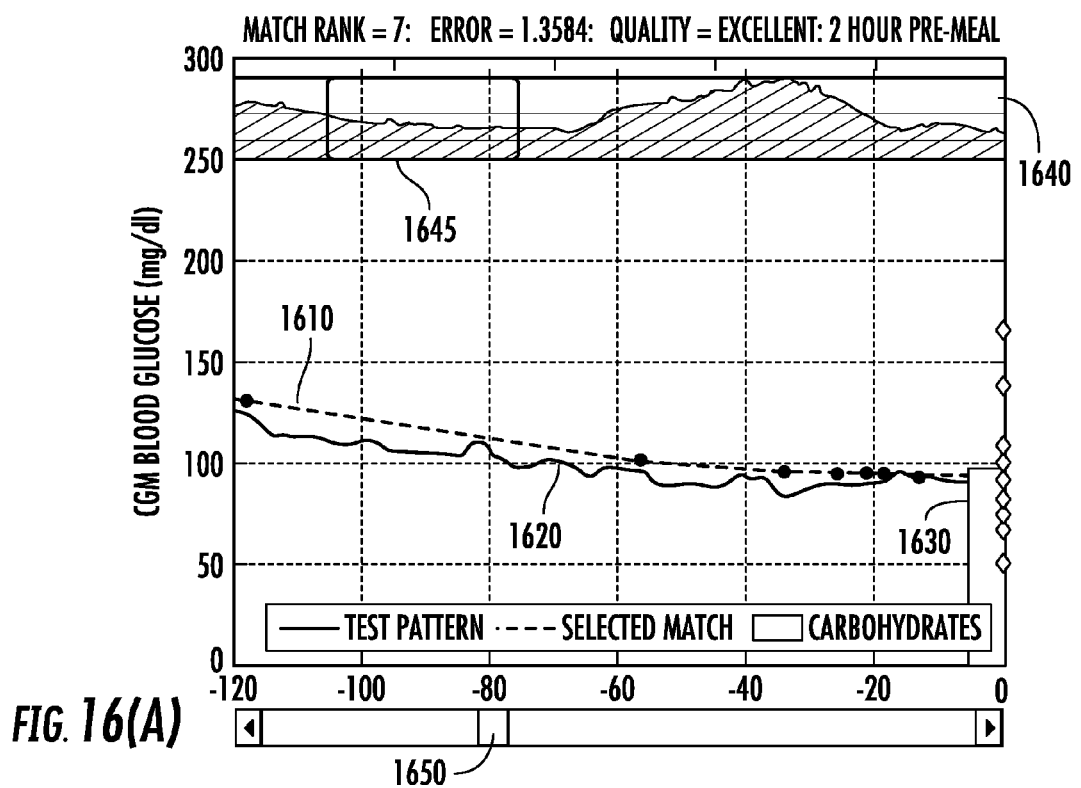
FIGS. 16(a)-16(e) depict exemplary displays of pattern match plots over a 2 hour time period.

FIG. 16(a) depicts an exemplary display of a reference pattern plot of blood glucose concentration over time and includes matching with a meal time tag. In this example, matches 1620 were determined for the two hours of data just prior to a meal in order to assist the user to evaluate possible outcomes for a meal based on past behaviors. Shown in FIG. 16(a) is the carbohydrates value for the meal. By way of example only, pattern matching may be done using a reference pattern 1610, a meal time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match. In this example, the actual outcome of the meal may be seen. Reference pattern 1610 was drawn and the pattern matching algorithm returned the top matches 1620. As depicted, the plot contains the reference pattern 1610 and the $7^{th}$ best match 1620. Of course, the plot may contain the reference pattern and one or more matches. Also, shown is a scroll bar 1650 at the bottom of the screen that may be used to scroll through and/or select a specific match. The scroll bar 1650 may be a touch sensitive display, whereby the scroll bar on the screen is touched with a finger and then moving the finger in a desired direction on the screen. The arrows to the left and right of scroll bar 1650 may be touched with a finger on the screen to scroll through and/or select a specific match. In addition, a mouse may also be used to scroll through using scroll bar 1650 or the left and right arrows. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 16B:
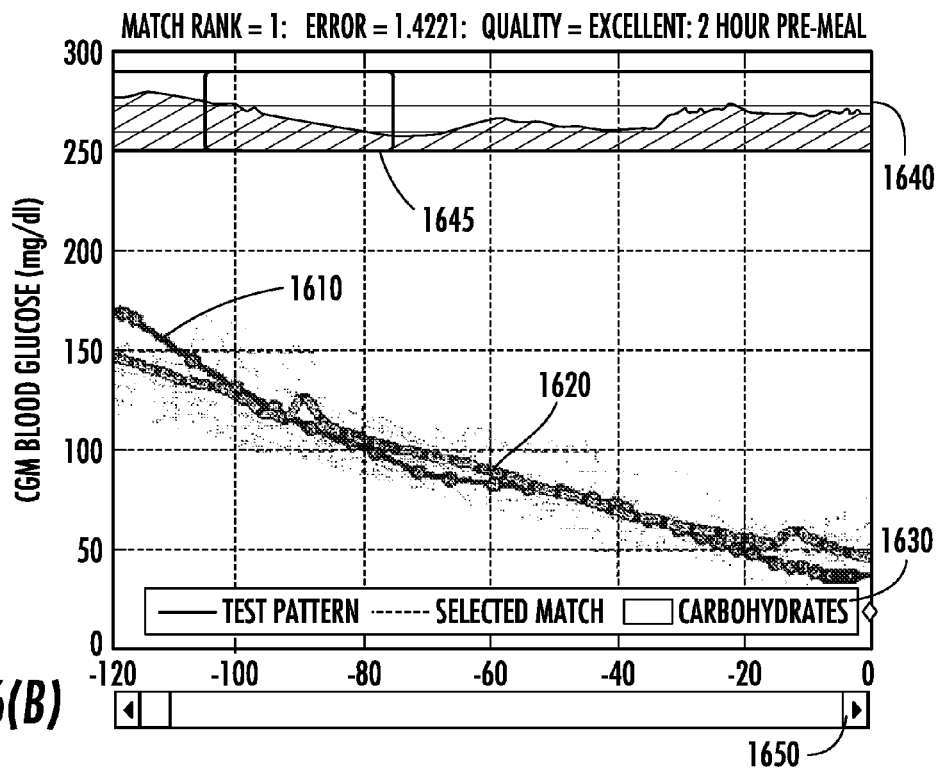

FIG. 16(b) depicts an exemplary display of a reference pattern plot of blood glucose concentration over time and includes matching with a meal time tag. In this example, the reference pattern 1610 is drawn to find instances of when a user may have been going into hypoglycemia and/or took carbohydrates to correct for the hypoglycemia. The display may be used to evaluate a patient's ability to correctly recover from hypoglycemia without overshooting into hyperglycemia. Matches 1620 were determined for two hours of data. The carbohydrates value (not shown) for the meal can be plotted. By way of example only, pattern matching may be done using a reference pattern 1610, meal time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match 1620. In this example, the actual outcome of the meal may be seen. Reference pattern 1610 was drawn and the pattern matching algorithm returned the top matches. As depicted, the plot contains the reference pattern 1610 and the best match 1620. Of course, the plot may contain the reference pattern 1610 and one or more matches 1620. Also, shown is a scroll bar 1650 at the bottom of the screen that may be used to scroll through and/or select a specific match 1620. The display also includes a match rank, which ranks the matches in order from closest to Nth closest match, where N is the number of matches. In this particular example, FIG. 16(b) shows a match rank of 1 indicating that the highlighted match is the closest match to the reference pattern. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 16C:
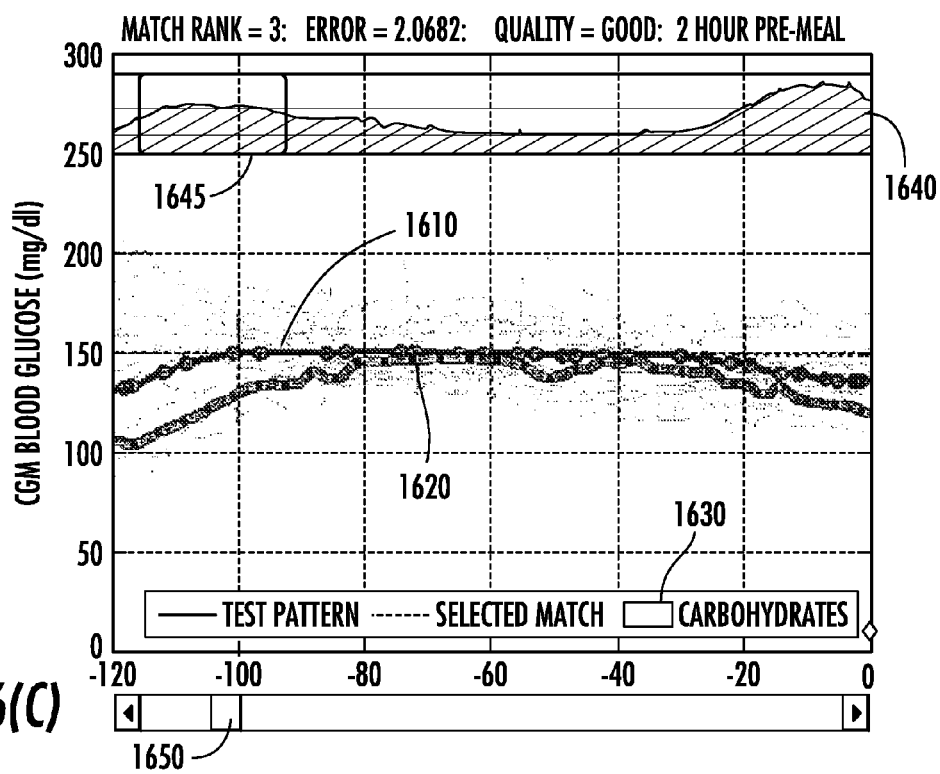

FIG. 16(c) depicts an exemplary display of a reference pattern plot of blood glucose concentration over time and includes matching with a sleep time tag. In this example, the reference pattern 1610 is selected for the two hour period prior to a subject going to sleep. The display may be used to evaluate the likelihood of nocturnal hypoglycemia based on the current state of the patient and their historical data. Matches 1620 were determined for two hours of data. The carbohydrates value (not shown) can be plotted. By way of example only, pattern matching may be done using a reference pattern 1610, sleep time tag and/or a carbohydrate value 1630. The display may include a timeline 1640 at the top of the reference pattern plot, which depicts the 2 hour matched section 1645 placed in a timeline with data shown on either side of matched section 1645 that may provide context of the match 1620. Reference pattern 1610 was selected and the pattern matching algorithm returned the top matches. As depicted, the plot contains the reference pattern 1610 and a match 1620. Of course, the plot may contain the reference pattern 1610 and one or more matches 1620. Also, shown is a scroll bar 1650 at the bottom of the screen that may be used to scroll through and/or select a specific match 1620. The display also includes a match rank, which ranks the matches in order from closest to Nth closest match, where N is the number of matches. In this particular example, FIG. 16(b) shows a match rank of 3 indicating that the highlighted match is the third closest match to the reference pattern. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 16D:
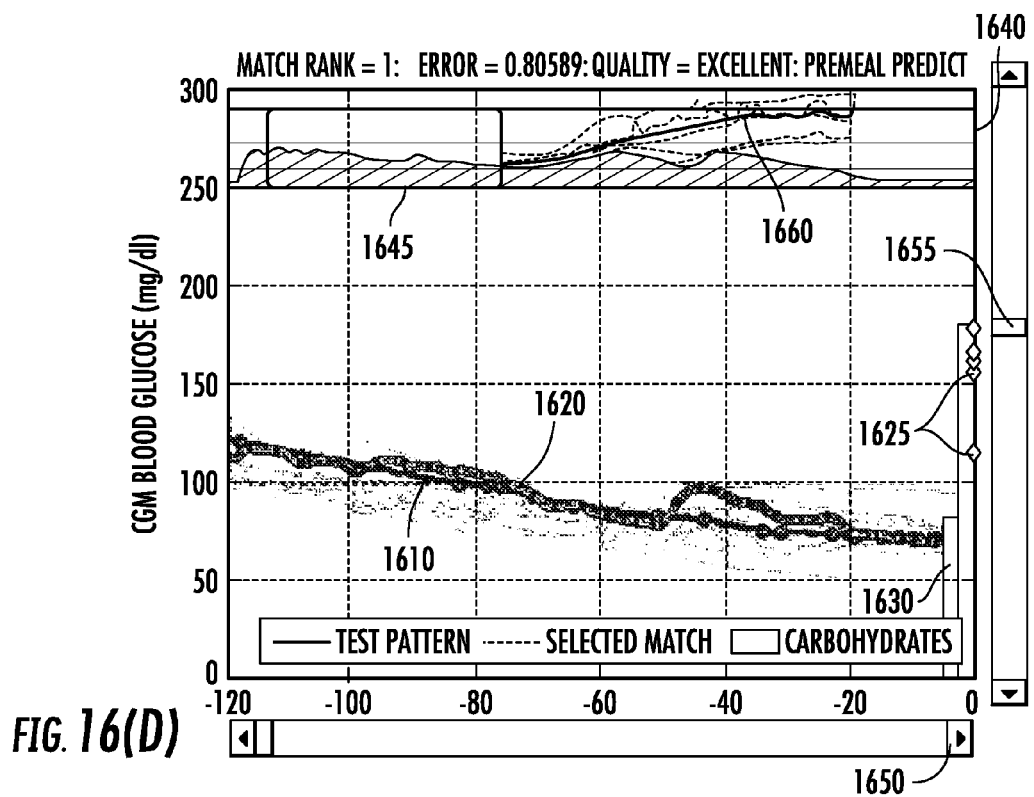
Figure 16E:
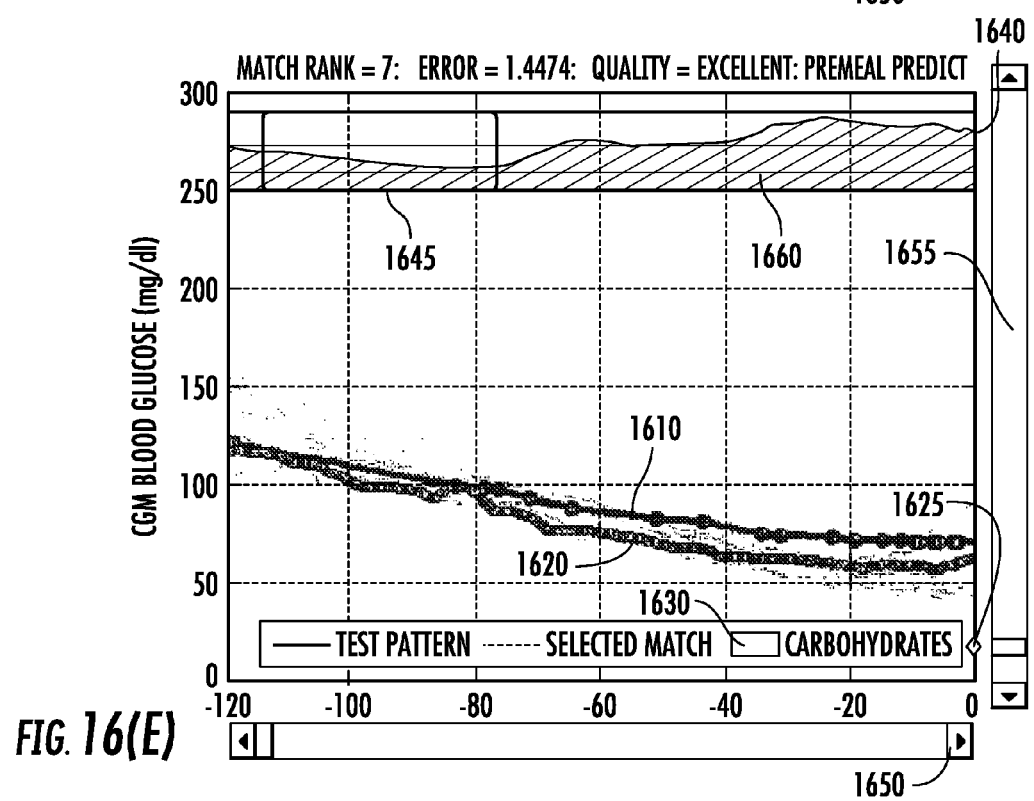

FIGS. 16(d) and 16(e) depict exemplary displays of a reference pattern plot of blood glucose concentration over time and includes matching using glucose levels, meal time tags, and carbohydrate values. Predictions of future glucose concentrations can be generated based on the matched data. The two figures depict a reference pattern 1610 with two different carbohydrate levels 1630 (shown only in FIG. 16(d)). The reference pattern 1610 and carbohydrate levels 1630 may be used to predict future blood glucose levels 1660, which are depicted in the timeline 1640. In this example, the reference pattern 1610 are selected for the two hour period prior to a meal. Reference pattern matches 1620 and carbohydrate matches 1625 were determined and plotted using the pattern matching algorithm. By way of example only, pattern matching may be done using a reference pattern 1610, glucose levels, meal time tags, and/or the current carbohydrate value 1630 that is being displayed. The displays shown include a timeline 1640 at the top of the reference pattern plot, which depicts the 2 hour matched section 1645 placed in a timeline with data shown on either side of matched section 1645 that may provide context of the match 1620. As mentioned above, timeline 1640 may also depict future blood glucose level predictions 1660. Also, shown is a horizontal scroll bar 1650 at the bottom of the screen that may be used to view the entire plot and/or scroll through matches. A vertical scroll bar 1655 may be used to scroll through and select or set the desired carbohydrate value 1630 to include in the reference pattern 1610. It may also be used to select a specific match 1620. The scroll bar 1655 may be a touch sensitive display, whereby the scroll bar on the screen is touched with a finger and then moving the finger in a desired direction on the screen. The arrows above and below scroll bar 1655 may be touched with a finger on the screen to scroll through and/or select a specific match. In addition, a mouse may also be used to scroll through using scroll bar 1655 or the up and down arrows. Quality of a match may be evaluated using error metrics (e.g., the absolute error between the match and the reference pattern), and a quality assessment label, for e.g., excellent, good, fair, poor, bad, awful, etc. or any other label that may be used to indicate the quality of a match.

Figure 17:
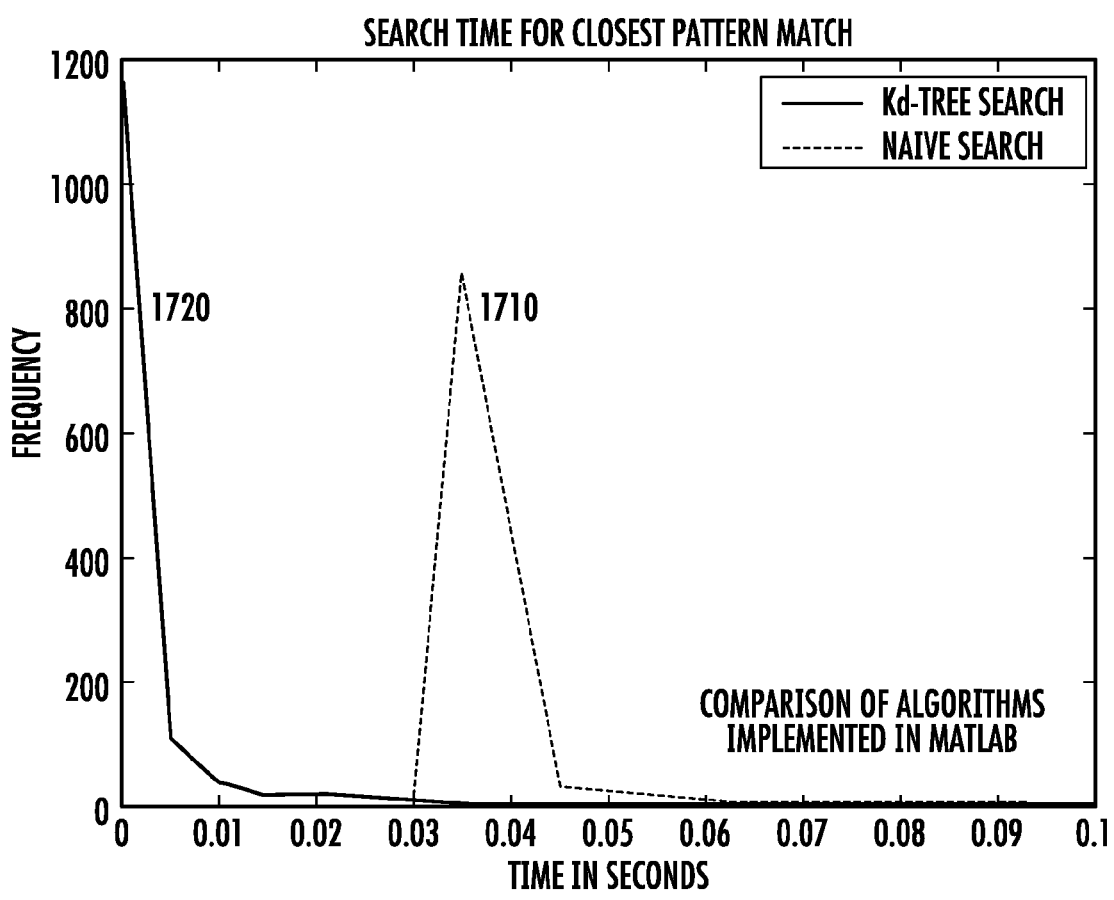
FIG. 17 depicts an exemplary plot of average search time in a pattern matching process.

FIG. 17 depicts an exemplary plot of the average search time for finding the closest match in the reduced-rank space when using two algorithms: a naïve exhaustive search 1710 and the kd-tree search 1720. Both algorithms may be used for searches and may be relatively efficient due to the compression algorithm; however, in this example, the kd-tree search 1720 significantly reduced the search time from an average of about 0.038 seconds to less than about 0.005 seconds.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and understood not to be limited to the details of structure and operation shown and described in the specification and drawings.

What is claimed is:

1. A method for real-time identification of a diabetes-related event in a patient using a monitoring system comprising a physiological data input device, a user input device and a processor, the method comprising:

receiving automatically from the user input device at least one reference pattern and associated alert signal;

receiving automatically from the physiological data input device at least one time window data set indicative of a physiological measurement related to the diabetes-related event;

associating automatically using the processor the at least one time window data set with a data tag;

transforming automatically using the processor the associated at least one time window data set into a normalized at least one time window data set, wherein the normalized at least one time window data set has a mean of zero and a standard deviation of one;

compressing automatically using the processor the normalized at least one time window data set into a compressed at least one time window data set;

storing automatically using the processor the compressed at least one time window data set; and pattern matching automatically using the processor between the reference pattern and the stored at least one time window data set using a distance metric, wherein when the distance metric is less than $\epsilon$, the processor automatically triggers the alert.

2. The method of claim 1, further comprising:

transforming automatically using the processor the reference pattern into a normalized reference pattern, wherein the normalized reference pattern has a mean of zero and a standard deviation of one, and compressing automatically using the processor the normalized reference pattern into a compressed reference pattern.

3. The method of claim 1, wherein $\epsilon$ is selected so that the probability that the matches are measurements of the same physiological data is at least about 0.95.

4. The method of claim 1, wherein $\epsilon$ is selected so that the probability that the matches are measurements of the same physiological data is at least about 0.98.

5. The method of claim 1, wherein the distance metric is a Euclidean distance.

6. The method of claim 1, wherein the compressed at least one time window data set is compressed automatically by the processor into a reduced-rank space by performing an eigen-decomposition via decomposing an $\hat{X}^T \hat{X}$ matrix into $\lambda$ eigenvalues and V eigenvectors.

7. The method of claim 6 further comprising automatically calculating using the processor the cumulative sum of the eigenvalues, determining the corresponding eigenvector for each eigenvalue, and selecting a subset of eigenvectors by balancing between data compression and preservation of relevant information.

8. The method of claim 7 further comprising automatically applying using the processor an orthogonal transform matrix to said subset of eigenvectors to provide a compressed reduced-rank vector.

* * * * *